(12) United States Patent
Chavali et al.

(10) Patent No.: US 12,178,172 B2
(45) Date of Patent: Dec. 31, 2024

(54) METHODS FOR IDENTIFYING CROSSES FOR USE IN PLANT BREEDING

(71) Applicant: Monsanto Technology LLC, Saint Louis, MO (US)

(72) Inventors: Srinivas Phani Kumar Chavali, Saint Louis, MO (US); Sambarta Dasgupta, Saint Louis, MO (US); Nalini Polavarapu, Saint Louis, MO (US)

(73) Assignee: MONSANTO TECHNOLOGY LLC, Saint Louis, MO (US)

( * ) Notice: Subject to any disclaimer, the term of this patent is extended or adjusted under 35 U.S.C. 154(b) by 0 days.

(21) Appl. No.: 18/138,716

(22) Filed: Apr. 24, 2023

(65) Prior Publication Data

US 2023/0255155 A1  Aug. 17, 2023

Related U.S. Application Data

(63) Continuation of application No. 16/448,334, filed on Jun. 21, 2019, now Pat. No. 11,632,920, which is a
(Continued)

(51) Int. Cl.
*G06F 7/00* (2006.01)
*A01H 1/02* (2006.01)
(Continued)

(52) U.S. Cl.
CPC .............. *A01H 1/04* (2013.01); *A01H 1/02* (2013.01); *G06N 7/01* (2023.01); *G06N 20/00* (2019.01); *G06N 20/20* (2019.01)

(58) Field of Classification Search
CPC . A01H 1/04; A01H 1/02; G06N 20/20; G06N 20/00; G06N 7/01
(Continued)

(56) References Cited

U.S. PATENT DOCUMENTS

| 6,285,999 B1 | 9/2001 | Page |
| 7,269,587 B1 | 9/2007 | Page |

(Continued)

FOREIGN PATENT DOCUMENTS

| WO | WO2013/026085 | 2/2013 |
| WO | WO2016/025848 | 2/2016 |

(Continued)

OTHER PUBLICATIONS

Akdemir, Deniz, and Julio I. Sanchez. "Efficient breeding by genomic mating." *Frontiers in genetics* 7 (2016), 11 pages.
(Continued)

*Primary Examiner* — Isaac M Woo
(74) *Attorney, Agent, or Firm* — Harness, Dickey & Pierce, P.L.C.

(57) ABSTRACT

Exemplary methods for use in identifying crosses for use in plant breeding are disclosed. One exemplary method includes generating population prediction scores for each potential cross within a set of potential crosses, where each population prediction score is associated with a prediction of commercial success for the associated potential cross within the set of potential crosses. The method also includes selecting a subgroup of potential crosses, based on thresholds associated with the population prediction scores for the set of potential crosses. The exemplary method further includes selecting multiple target crosses from the subgroup of potential crosses based on a genetic relatedness of the parents in the subgroup of potential crosses, and directing ones of the selected target crosses into a breeding pipeline, thereby providing crosses to the breeding pipeline based, at least in part, on commercial success of parents included in the selected ones of the filtered crosses.

20 Claims, 13 Drawing Sheets

Related U.S. Application Data continuation of application No. 15/618,023, filed on Jun. 8, 2017, now Pat. No. 10,327,400.

(60) Provisional application No. 62/347,344, filed on Jun. 8, 2016.

(51) Int. Cl.
| | |
|---|---|
| *A01H 1/04* | (2006.01) |
| *G06N 7/01* | (2023.01) |
| *G06N 20/00* | (2019.01) |
| *G06N 20/20* | (2019.01) |

(58) Field of Classification Search
USPC .................................. 707/600–899; 800/260
See application file for complete search history.

(56) References Cited

U.S. PATENT DOCUMENTS

| | | | |
|---|---|---|---|
| 9,727,639 | B2 | 8/2017 | Groeneveld et al. |
| 9,727,926 | B2 | 8/2017 | Napper et al. |
| 9,734,239 | B2 | 8/2017 | Allen et al. |
| 10,327,400 | B2 | 6/2019 | Chavali et al. |
| 11,632,920 | B2 | 4/2023 | Chavali et al. |
| 2005/0144664 | A1 | 6/2005 | Smith et al. |
| 2007/0083456 | A1 | 4/2007 | Akers |
| 2010/0100980 | A1 | 4/2010 | Bull et al. |
| 2011/0179020 | A1 | 7/2011 | Ozzie et al. |
| 2011/0224911 | A1 | 9/2011 | Ostrander et al. |
| 2012/0151625 | A1* | 6/2012 | Guo ....................... G16B 20/40 |
| | | | 435/410 |
| 2013/0117878 | A1 | 5/2013 | Bink et al. |
| 2013/0340110 | A1 | 12/2013 | Robbins et al. |
| 2014/0130200 | A1 | 5/2014 | Bliss |
| 2015/0080238 | A1 | 3/2015 | Ragot et al. |
| 2017/0156276 | A1 | 6/2017 | Bull et al. |
| 2017/0223947 | A1 | 8/2017 | Gall et al. |
| 2017/0295735 | A1 | 10/2017 | Butruille et al. |
| 2017/0354105 | A1 | 12/2017 | Polavarapu et al. |
| 2019/0174691 | A1 | 6/2019 | Chavali et al. |
| 2019/0180845 | A1 | 6/2019 | Chavali et al. |

FOREIGN PATENT DOCUMENTS

| | | |
|---|---|---|
| WO | WO2016022517 | 2/2016 |
| WO | WO2017/214445 | 12/2017 |
| WO | WO2019/113468 | 6/2019 |
| WO | WO2019/113480 | 6/2019 |

OTHER PUBLICATIONS

Bishop, Christopher M., Pattern recognition and machine learning, Springer (2006) 758 pages.

Bollabas. Bela, Graduate Texts in Mathematics, Modern graph theory.vol. 184. Springer Science & Business Media, 2013, 409 pages.

Ensemble Methods in Data Mining: Improving Accuracy Through Combining Predictions, Giovanni Seni and John Elder, 2010 (Morgan and Claypool Publishers), 126 pages.

Ensemble-based classifiers, Rokach (2010), Artificial Intelligence Review 33(1-2): 1-39.

Fernández-Madrigal, J-A., and Javier González. "Multihierarchical graph search." *IEEE Transactions on Pattern Analysis and Machine Intelligence* 24.1 (2002): 103-113.

Fortunato, Santo. "Community detection in graphs." *Physics reports* 486.3 (2010): 75-174.

Greg Linden, Brent Smith and Jeremy York. Amazon.com recommendations: Item-to-item collaborative filtering. IEEE Internet Computing, 7(1): 76-80, 2003.

Han, Ye, et al. "The Predicted Cross Value for Genetic Introgression of Multiple Alleles." *Genetics* 205.4 (2017): 1409-1423.

Isidro, Julio, et al. "Training set optimization under population structure in genomic selection." *Theoretical and applied genetics* 128.1 (2015): 145-158.

Jure Leskovec, Lada A. Adamic, and Bernardo A. Huberman. The dynamics of viral marketing. ACM Transactions on the web (ACMTWEB), 1(1), 2007, 39 pages.

Lars Backstrom and Jure Leskovec. Supervised random walks: Predicting and recommending links in social networks. Proceeding of WSDM 2011, pp. 635-644, 2011.

Li, Xin, and Hsinchun Chen. "Recommendation as link prediction in bipartite graphs: A graph kernel-based machine learning approach." Decision Support Systems 54.2 (2013): 880-890.

Mirza, Batul J., Benjamin J. Keller, and Naren Ramakrishnan. "Studying recommendation algorithms by graph analysis." Journal of Intelligent Information Systems 20.2 (2003): 131-160.

Murphy, Kevin P., Machine learning: a probabilistic perspective (MIT press, 2012), 1105 pages.

Popular ensemble methods: An empirical study, Opitz & Maclin (1999), Journal of Artificial Intelligence Research 11: 169-98.

Stanford large network dataset collection. http://snap.stanford.edu/data/index.html. accessed Nov. 2017, 5 pages.

Tao Zhou, Jie Ren, Matus Medo, and Yi-Chen Zhang. Bipartite network projection and personal recommendation. Physical Review E, 2007, 8 pages.

Thulasiraman, Krishnaiyan, and Madisetti NS Swamy. Graphs: theory and algorithms.John Wiley & Sons, 2011, 470 pages.

Wasserman, Stanley, and Katherine Faust. *Social network analysis: Methods and applications.* vol. 8. Cambridge university press (1994), 116 pages.

Faux, Anne-Michelle et al., "AlphaSim: Software for Breeding Program Simulation", The Plant Genome, vol. 9, No. 3, Nov. 2016 (published Sep. 22, 2016), pp. 1-14.

Lado, Bettina et al., "Strategies for Selecting Crosses Using Genomic Prediction in Two Wheat Breeding Programs", The Plant Genome, vol. 10, No. 2, Jul. 2017 (published Jul. 13, 2017), pp. 1-13.

Charcosset, A. et al., "Prediction of Maize Hybrid Silage Performance Using Marker Data: Comparison of Several Models for Specific Combining Ability", Crop Science, vol. 38, No. 1, Jan. 1998, pp. 38-44.

Xu, S. et al., "Predicting hybrid performance in rice using genomic best linear unbiased prediction", Proceedings of the National Academy of Sciences, vol. 111, No. 34, Aug. 2014, pp. 12456-12461.

Sun X et al. The role and basics of computer simulation in support of critical decisions in plant breeding. Molecular Breeding. Kluwer Academic Publishers, vol. 28, No. 4, Sep. 10, 2011, pp. 421-436.

Jannink et al., Genomic selection in plant breeding: from theory to practice. Briefings in Functional Genomics, vol. 9, No. 2, Feb. 15, 2010, pp. 166-177.

Ivandro Bertan et al.. Parental Selection Strategies in Plant Breeding Programs, Journal of Crop Science and Biotechnology, vol. 10, No. 4, Jan. 1, 2007, pp. 211-222.

Ex Parte Reexamination Proceeding for U.S. Pat. No. 10,327,400 (U.S. Appl. No. 90/019,225): Ex Parte Request for Reexamination, 104 pages (Jul. 6, 2023).

Declaration of Lizhi Wang, PhD, cited in Ex Parte Request for Reexamination of U.S. Pat. No. 10,327,400 (Exhibit 10), 32 pages (Jun. 27, 2023).

Ex Parte Reexamination Proceeding for U.S. Pat. No. 10,327,400 (U.S. Appl. No. 90/019,225): Reexamination Order, 19 pages (Aug. 24, 2023).

Ex Parte Reexamination Proceeding for U.S. Pat. No. 10,327,400 (U.S. Appl. No. 90/019,225): Reexamination Non-Final Office Action, 19 pages (Jan. 24, 2024).

Ex Parte Reexamination Proceeding for U.S. Pat. No. 10,327,400 (U.S. Appl. No. 90/019,225): Patent Owner's Response to Non-Final Office Action, 31 pages (Mar. 23, 2024).

Ex Parte Reexamination Proceeding for U.S. Pat. No. 10,327,400 (U.S. Appl. No. 90/019,225): Notice of Intent to Issue Reexam Certificate (all claims patentable), 4 pages (Apr. 12, 2024).

Ramdoyal, K. et al., "Sugar Cane Hybridization Procedures and Computer-aided Crossing at the Mauritius Sugar Industry Research Institute." Sugar Cane. pp. 5-10 (Sep. 1999).

(56) References Cited

OTHER PUBLICATIONS

Zhong, S. and Jannink, J., "Using Quantitative Trait Loci Results to Discriminate Among Crosses on the Basis of Their Progeny Mean and Variance." Genetics. 177:567-576 (2007).
Monteith, K. et al., "Turning Bayesian Model Averaging into Bayesian Model Combination." The 2011 International Joint Conference on Neural Networks. 2657-2663 (2011).
Boppenmaier, J. et al., "Genetic Diversity for RFLPs in European Maize Inbreds: III. Performance of Crosses Within Versus Between Heterotic Groups for Grain Traits." Plant Breeding. 111: 217-226 (1993).
Ji, D. et al., "An Improved Decision Tree Algorithm and Its Application in Maize Seed Breeding." 2010 Sixth International Conference on Natural Computation. vol. 1. IEEE (2010).
Butruille, D. et al., Chapter 5 "Maize Breeding in the United States: Views from Within Monsanto." Plant Breeding Reviews, vol. 39, First Edition. John Wiley & Sons, Inc., 84 pages (2015).
Akdemir, D. and Julio I. Sánchez. "Efficient Breeding by Genomic Mating." BioRxiv preprint, 15 pages (Feb. 8, 2016).

\* cited by examiner

| A | B | C | D | E | F | G | H | I | J |
|---|---|---|---|---|---|---|---|---|---|
| P1 | P2 | ORIGIN | P1_SELIN_blup | P2_SELIN_blup | P1_YLD_BE_blup | P2_YLD_BE_blup | P1_MST_blup | P2_MST_blup | P1_SELTM_blup |
| L_592 | L_1460 | L_592/L_1460 | 101.47 | 106.16 | 103.31 | 102.38 | 110.73 | 96.76999 | 102.86 |
| L_349 | L_1460 | L_349/L_1460 | 103.31 | 106.16 | 104.22 | 102.38 | 110.62 | 96.76999 | 104.57 |
| L_638 | L_1460 | L_638/L_1460 | 101.24 | 106.16 | 104.71 | 102.38 | 113.83 | 96.76999 | 103.28 |
| L_33 | L_1434 | L_33/L_1434 | 109.41 | 98.12 | 104.98 | 98.31 | 103.95 | 105.48 | 106.94 |
| L_532 | L_1482 | L_532/L_1482 | 107.43 | 101.29 | 106.47 | 100.09 | 116 | 95.12999 | 107.08 |
| L_125 | L_1220 | L_125/L_1220 | 106.28 | 103.63 | 106.3 | 102.88 | 107.98 | 102.75 | 108.37 |
| L_248 | L_1343 | L_248/L_1343 | 113.28 | 102.24 | 106.14 | 103.05 | 107.99 | 96.43999 | 109.56 |
| L_7 | L_1434 | L_7/L_1434 | 105.82 | 98.12 | 101.56 | 98.31 | 101.33 | 105.48 | 101.89 |
| L_8 | L_1434 | L_8/L_1434 | 108.49 | 98.12 | 102.55 | 98.31 | 102.04 | 105.48 | 104.66 |
| L_9 | L_1434 | L_9/L_1434 | 108.41 | 98.12 | 103.8 | 98.31 | 104.25 | 105.48 | 104.37 |
| L_1 | L_1434 | L_1/L_1434 | 121.01 | 98.12 | 110.98 | 98.31 | 106.77 | 105.48 | 115.18 |
| L_2 | L_1434 | L_2/L_1434 | 107.98 | 98.12 | 104.74 | 98.31 | 101.4 | 105.48 | 108.14 |
| L_3 | L_1434 | L_3/L_1434 | 110.85 | 98.12 | 105.51 | 98.31 | 105.41 | 105.48 | 108.74 |

FIG. 3A

| K | L | M | N | O | P | Q | R | S | T |
|---|---|---|---|---|---|---|---|---|---|
| P2_SELTM_blup | P1_TWT_blup | P2_TWT_blup | P1_RTLP_blup | P2_RTLP_blup | P1_AVG_SCORE_PS1 | P2_AVG_SCORE_PS1 | P1_PR_ADV | P2_PR_ADV | SIMILARITY |
| 105.31 | 102.63 | 100.78 | 113.69 | 55.22999 | 0.27961 | 0.424438 | 0.310456 | 0.533895 | 0.804 |
| 105.31 | 98.93 | 100.78 | 3.83999 | 55.22999 | 0.300652 | 0.424438 | 1.226449 | 0.533895 | 0.786 |
| 105.31 | 96.73 | 100.78 | 82.7 | 55.22999 | 0.844975 | 0.424438 | 0.290741 | 0.533895 | 0.834 |
| 96.15999 | 98.78 | 99.17 | 70.87999 | 78.14 | 0.225776 | 0.124337 | 0.385561 | -2.83942 | 0.808 |
| 102.65 | 99.64 | 101.05 | 345.5 | 42.63 | 0.290013 | 0.078833 | 0.87093 | 0.071996 | 0.733 |
| 104.91 | 99.60999 | 99.56 | 198.81 | 125.09999 | 1.214113 | 1.03297 | 1.094368 | 0.517935 | 0.748 |
| 102.97 | 99.9 | 100.67 | 149.11 | 163.3 | 0.71885 | 0.778207 | 0.8315 | 0.151796 | 0.819 |
| 96.15999 | 97.98 | 99.17 | 94.48 | 78.14 | -0.00249 | 0.124337 | 0.248861 | -2.83942 | 0.908 |
| 96.15999 | 97.68 | 99.17 | 97.26 | 78.14 | 0.21384 | 0.124337 | 0.725413 | -2.83942 | 0.652 |
| 96.15999 | 99.84 | 99.17 | 133.91 | 78.14 | 0.122088 | 0.124337 | 0.612755 | -2.83942 | 0.881 |
| 96.15999 | 98.40999 | 99.17 | 136.79 | 78.14 | 0.471919 | 0.124337 | 0.788314 | -2.83942 | 0.75 |
| 96.15999 | 101.12 | 99.17 | 160.02 | 78.14 | 1.390488 | 0.124337 | 0.801106 | -2.83942 | 0.82 |
| 96.15999 | 98.84 | 99.17 | 68.45999 | 78.14 | -1.4672 | 0.124337 | -1.52115 | -2.83942 | 0.893 |

FIG. 3B

| U | V | W | X | Y | Z | AA | BB | CC | DD | EE | FF |
|---|---|---|---|---|---|---|---|---|---|---|---|
| P1_CLUSTER | P2_CLUSTER | ORIGIN_CLUSTER_INDEX | MicPar_Model | P1_BlupModel | P2_BlupModel | CODE_YR1 | CODE_YR2 | P1_TOT_HYBRIDS | P2_TOT_HYBRIDS | TOT_HYBRIDS | RTLP_blup |
| 3 | 1 | M_1_3 | 0.151111 | 0.22 | 0.303333 | 2013 | 2013 | 7 | 3 | 10 | 84.450995 |
| 3 | 1 | M_1_3 | 0.333333 | 0.266667 | 0.303333 | 2012 | 2013 | 175 | 3 | 178 | 29.53499 |
| 3 | 1 | M_1_3 | 0.268889 | 0.282222 | 0.303333 | 2012 | 2013 | 25 | 3 | 28 | 68.964995 |
| 7 | 2 | F_2_7 | 0.207778 | 0.543333 | 0.341111 | 2010 | 2004 | 133 | 0 | 133 | 74.509995 |
| 2 | 1 | F_1_2 | 0.198667 | 0.252222 | 0.17 | 2013 | 2012 | 65 | 36 | 101 | 194.065 |
| 2 | 1 | F_1_2 | 0.413333 | 0.384444 | 0.364444 | 2014 | 2013 | 11 | 13 | 24 | 161.954995 |
| 3 | 3 | M_3_3 | 0.586667 | 0.607778 | 0.265556 | 2015 | 2014 | 6 | 8 | 14 | 156.205 |
| 2 | 2 | F_2_2 | 0.238889 | 0.401111 | 0.341111 | 2015 | 2004 | 6 | 0 | 6 | 86.31 |
| 2 | 2 | F_2_2 | 0.375556 | 0.42 | 0.341111 | 2015 | 2004 | 6 | 0 | 6 | 87.7 |
| 2 | 2 | F_2_2 | 0.336667 | 0.503333 | 0.341111 | 2015 | 2004 | 6 | 0 | 6 | 106.025 |
| 1 | 2 | F_1_2 | 0.334444 | 0.511111 | 0.341111 | 2015 | 2004 | 0 | 0 | 0 | 107.464995 |
| 7 | 2 | F_2_7 | 0.2 | 0.462222 | 0.341111 | 2013 | 2004 | 0 | 0 | 0 | 119.08 |
| 7 | 2 | F_2_7 | 0.253333 | 0.715556 | 0.341111 | 2014 | 2004 | 0 | 0 | 0 | 73.299995 |

| GG | HH | II | JJ | KK | LL | MM | NN | OO | PP | QQ | RR |
|---|---|---|---|---|---|---|---|---|---|---|---|
| STLP_blub | GW_PRED | P1_Standability | P2_Standability | P1_Per | P2_Per | AgeSimModel | advScore | Per_Strata_Bin | P1_perfMetric | P1_riskMetric | P2_perfMetric |
| 89.34999 | 5.417118104 | 0.371111 | 0.435556 | 0.391111 | 0.294444 | 0.673333 | 0.524656 | 4 | 0.467338 | 0.813311 | 0.334986 |
| 88.824995 | 5.195981148 | 0.446667 | 0.435556 | 0.52 | 0.294444 | 0.494444 | 0.542413 | 4 | 0.606879 | 0.182986 | 0.334986 |
| 99.674995 | 4.881936298 | 0.184444 | 0.435556 | 0.315556 | 0.294444 | 0.754444 | 0.471146 | 5 | 0.444829 | 0.503829 | 0.334986 |
| 98.015005 | 4.297113303 | 0.57 | 0.361111 | 0.437778 | NA | 0.227778 | 0.481433 | 6 | 0.586608 | 0.023719 | 0.064615 |
| 100.414995 | 5.043199706 | 0.466667 | 0.651111 | 0.383333 | 0.305556 | 0.291111 | 0.525361 | 5 | 0.497091 | 0.505943 | 0.349186 |
| 83.32499 | 4.608332419 | 0.701111 | 0.428889 | 0.324444 | 0.306667 | 0.807778 | 0.527194 | 3 | 0.601697 | 0.789827 | 0.373716 |
| 175.579995 | 3.640910067 | 0.221111 | 0.211111 | 0.516667 | 0.341111 | 0.98 | 0.673113 | 2 | 0.67025 | 0.834853 | 0.389313 |
| 92.5 | 4.557144832 | 0.466667 | 0.361111 | 0.298889 | NA | 0.45 | 0.433325 | 6 | 0.306627 | 0.834853 | 0.064615 |
| 82.564995 | 4.873403203 | 0.393333 | 0.361111 | 0.486667 | NA | 0.433333 | 0.502205 | 5 | 0.537358 | 0.834853 | 0.064615 |
| 86.454995 | 4.916038644 | 0.393333 | 0.361111 | 0.461111 | NA | 0.465556 | 0.503868 | 5 | 0.57073 | 0.834853 | 0.064615 |
| 113.98 | 4.443952811 | 0.27 | 0.361111 | NA | NA | 0.351111 | 0.686912 | 2 | 0.576434 | 1 | 0.064615 |
| 144.049995 | 4.900866319 | 0.294444 | 0.361111 | NA | NA | 0.335556 | 0.461496 | 6 | 0.515745 | 1 | 0.064615 |
| 84.52 | 4.291622581 | 0.387778 | 0.361111 | NA | NA | 0.452222 | 0.555569 | 4 | 0.354261 | 1 | 0.064615 |

FIG. 3D

| SS | TT | UU | V | WW | XX | YY | ZZ | AAA | BBB | CCC |
|---|---|---|---|---|---|---|---|---|---|---|
| P2_riskMetric | perfMetric | riskMetric | progeney-ClusterScore | CLUSTER_SCORES | PASS_CLUSTER_FILTERING | PASS_RULE_FILTER | PASS_OPTIM_1_FILTER | PASS_OPTIM_2_FILTER | PASS_OPTIM_3_FILTER | PASS_OPTIM_4_FILTER |
| 0.909252 | 0.230237 | 0.173178 | 0.083888889 | 0.256618897 | TRUE | TRUE | FALSE | FALSE | FALSE | FALSE |
| 0.909252 | 0.446407 | 0.037671 | 0.083888889 | 0.256618897 | TRUE | TRUE | FALSE | FALSE | FALSE | FALSE |
| 0.909252 | 0.22309 | 0.140828 | 0.083888889 | 0.256618897 | TRUE | TRUE | FALSE | FALSE | FALSE | FALSE |
| 0.494412 | 0.362667 | 0.030023 | 0.188888889 | 0.266810305 | TRUE | FALSE | FALSE | FALSE | FALSE | FALSE |
| 0.228317 | 0.3332 | 0.027015 | 0.022222222 | 0.26861953 | TRUE | FALSE | FALSE | FALSE | FALSE | FALSE |
| 0.708612 | 0.297923 | 0.102872 | 0.022222222 | 0.26861953 | TRUE | FALSE | FALSE | FALSE | FALSE | FALSE |
| 0.793064 | 0.31488 | 0.120867 | 0.277777778 | 0.264665312 | TRUE | FALSE | FALSE | FALSE | FALSE | FALSE |
| 0.494412 | 0.172195 | 0.118232 | 0.610434763 | 0.273882802 | FALSE | FALSE | FALSE | FALSE | FALSE | FALSE |
| 0.494412 | 0.214987 | 0.102424 | 0.610434763 | 0.273882802 | FALSE | FALSE | FALSE | FALSE | FALSE | FALSE |
| 0.494412 | 0.216872 | 0.101679 | 0.610434763 | 0.273882802 | FALSE | FALSE | FALSE | FALSE | FALSE | FALSE |
| 0.494412 | 0.296675 | 0.089327 | 0.022222222 | 0.26861953 | TRUE | FALSE | FALSE | FALSE | FALSE | FALSE |
| 0.494412 | 0.182688 | 0.132959 | 0.188888889 | 0.276810305 | FALSE | FALSE | FALSE | FALSE | FALSE | FALSE |
| 0.494412 | 0.231093 | 0.110445 | 0.188888889 | 0.276810305 | TRUE | FALSE | FALSE | FALSE | FALSE | FALSE |

FIG. 3E

| DDD | EEE |
|---|---|
| PASS_OPTIM_5 FILTER | COMMENTS |
| FALSE | OPTIMIZATION FILTER |
| FALSE | OPTIMIZATION FILTER |
| FALSE | OPTIMIZATION FILTER |
| FALSE | TRAIT FILTER (PARENT DROPPED) |
| FALSE | TRAIT FILTER (ROOT) |
| FALSE | TRAIT FILTER (ROOT) |
| FALSE | TRAIT RULE (STALK) |
| FALSE | GENETIC FILTER |
| FALSE | GENETIC FILTER |
| FALSE | GENETIC FILTER |
| FALSE | NO SEED |
| FALSE | NO SEED |
| FALSE | NO SEED |

FIG. 3F

METHODS FOR IDENTIFYING CROSSES FOR USE IN PLANT BREEDING

CROSS-REFERENCE TO RELATED APPLICATION

This application is a continuation of U.S. patent application Ser. No. 16/448,334, filed on Jun. 21, 2019, which is a continuation of U.S. patent application Ser. No. 15/618,023, filed on Jun. 8, 2017, which claims the benefit of and priority to U.S. Provisional Application No. 62/347,344, filed on Jun. 8, 2016. The entire disclosure of each of the above applications is incorporated herein by reference.

FIELD

The present disclosure generally relates to methods for use in plant breeding and in related breeding programs, and in particular to methods for use in identifying parents for creating new crosses for use in plant breeding and in related plant breeding programs.

BACKGROUND

This section provides background information related to the present disclosure which is not necessarily prior art.

In plant development, modifications are made in the plants, either through selective breeding or genetic manipulation. And, when a desirable improvement is achieved, a commercial quantity is developed by planting seeds from selected ones of the plants and harvesting resulting seeds over several generations. Throughout the process, numerous decisions are made based on characteristics and/or traits of the plants being bred, and similarly on characteristics and/or traits of their parents, although not all resulting crosses are guaranteed to inherit or exhibit the desired traits. Traditionally, as part of selecting particular plants for further development, samples are taken from the plants and/or their resulting seeds and tested so that only plants and/or seeds having the desired characteristics and/or traits are advanced. Plant development involves large numbers of possible crosses, from which final breeding decisions must be made.

DRAWINGS

The drawings described herein are for illustrative purposes only of selected embodiments and not all possible implementations, and are not intended to limit the scope of the present disclosure.

FIGS. 3A-3F illustrate an excerpt of an exemplary crosses data structure suitable for use with the system of FIG. 1;

Corresponding reference numerals indicate corresponding parts throughout the several views of the drawings.

DETAILED DESCRIPTION

Exemplary embodiments will now be described more fully with reference to the accompanying drawings. The description and specific examples included herein are intended for purposes of illustration only and are not intended to limit the scope of the present disclosure.

Various breeding techniques are commonly employed in agricultural industries to produce desired offspring. Often, breeding programs implement such techniques to obtain offspring having desired characteristics or combinations of characteristics (e.g., yield, disease resistance, etc.). However, it is difficult to accurately determine the best parents to cross when selecting a set of breeding starts, or origins, for such programs, especially when a large number of options are available. For example, a breeder given more than 1,000 male and/or female parental lines may identify several hundreds if not thousands of crosses with high potential of producing commercial products. What's more, crosses having desired characteristics or combinations of characteristics, while potentially performing well when planted in the field, may not necessarily be commercially successful for various reasons. Uniquely, the systems and methods herein are configured to select parents for use in breeding pipelines based on predicted commercial value of potential crosses between the parents, as determined from commercial success of the parents (and/or the parents' parents, and/or other members in the parental lines) in combination with relatedness and/or risks associated with the given crosses, and further relying on individual traits and/or characteristics of the parents (and/or the parents' parents, and/or other members in the parental lines). In this manner, a more complete picture of the potential crosses of the parents is provided, from which efficiency in selecting populations of crosses for the plant breeding pipelines can be gained.

Figure 1:
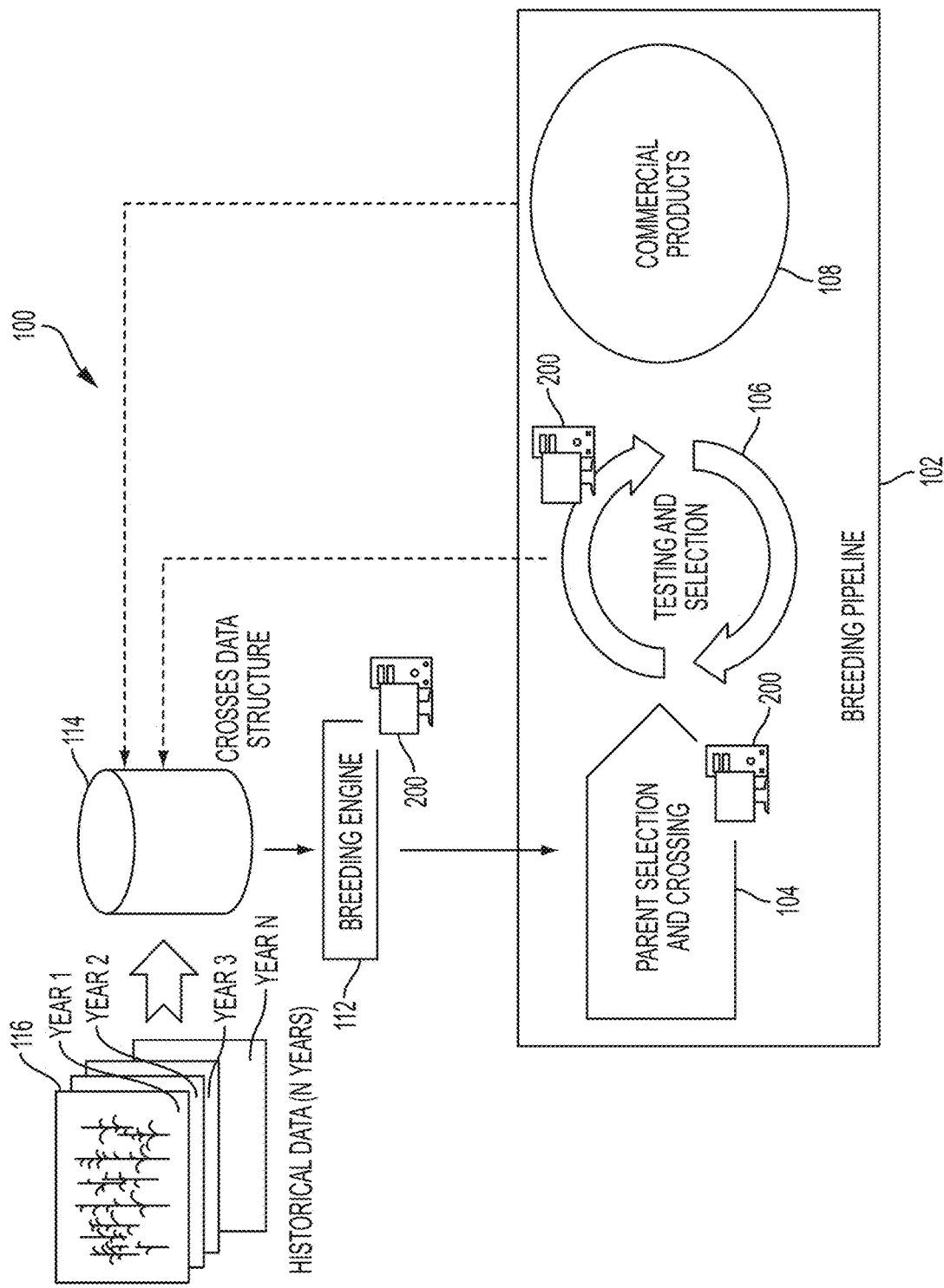
FIG. 1 is a block diagram of an exemplary system of the present disclosure suitable for identifying plant crosses for use in plant breeding.

With reference now to the drawings, FIG. 1 illustrates an exemplary system 100 for identifying crosses for use in breeding plants, in which the one or more aspect of the present disclosure may be implemented. Although, in the described embodiment, parts of the system 100 are presented in one arrangement, other embodiments may include the same or different parts arranged otherwise depending, for example, on particular plants being bred, particular characteristics and/or traits of interest, particular breeding techniques implemented, etc.

As shown in FIG. 1, the system 100 generally includes a breeding pipeline 102, which is provided to create new plants by crossing an existing pool of parents. In certain embodiments, the breeding pipeline 102 is employed to create commercial products by first crossing parent plants to produce offspring seed (and/or plants). The pipeline 102 generally defines a pyramidal progression, whereby it starts with a large number of potential crosses from parents, and keeps narrowing down to pick preferred and/or desired ones of the crosses. The pipeline 102 often involves identification of preferred performing populations from this large number of potential crosses, which typically involves subjecting the populations of offspring to rigorous testing using a wide range of methods known in the art. In certain breeding pipelines (e.g., large industrial breeding pipelines, etc.), this process may involve testing hundreds, thousands, or more crosses in multiple phases at several locations, over several years, to arrive at a reduced set of crosses selected for commercial product development. In short, the breeding pipeline 102 comprises many processes designed to reduce a large number of crosses down to a relatively few number of superior-performing commercial products.

In this exemplary embodiment, the breeding pipeline 102 is described with reference to, and is generally directed to, maize. However, it should be appreciated that the methods disclosed herein are not limited to maize and may be employed in a plant breeding pipeline/program relating to other plants, for example, to improve any fruit, vegetable, grass, tree, or ornamental crop, including, but not limited to, maize (*Zea mays*), soybean (*Glycine max*), cotton (*Gossypium hirsutum*), peanut (*Arachis hypogaea*), barley (*Hordeum vulgare*), oats (*Avena sativa*), orchard grass (*Dactylis glomerata*), rice (*Oryza sativa*, including indica and japonica varieties), sorghum (*Sorghum bicolor*), sugar cane (*Saccharum* sp), tall fescue (*Festuca arundinacea*), turfgrass species (e.g., species: *Agrostis stolonifera, Poa pratensis, Stenotaphrum secundatum*, etc.), wheat (*Triticum aestivum*), and alfalfa (*Medicago sativa*), members of the genus *Brassica*, including broccoli, cabbage, cauliflower, canola, and rapeseed, carrot, Chinese cabbage, cucumber, dry bean, eggplant, fennel, garden beans, gourd, leek, lettuce, melon, okra, onion, pea, pepper, pumpkin, radish, spinach, squash, sweet maize, tomato, watermelon, honeymelon, cantelope and other melons, banana, castorbean, coconut, coffee, cucumber, *Poplar*, Southern pine, *Radiata* pine, Douglas Fir, *Eucalyptus*, apple and other tree species, orange, grapefruit, lemon, lime and other citrus, clover, linseed, olive, palm, *Capsicum, Piper*, and *Pimenta* peppers, sugarbeet, sunflower, sweetgum, tea, tobacco, and other fruit, vegetable, tuber, and root crops. The methods herein may also be used in conjunction with non-crop species, especially those used as model systems, such as *Arabidopsis*, etc.

As shown in FIG. 1, the breeding pipeline 102 includes a parent selection and crossing phase 104 and a testing and selection phase 106, which together yield one or more commercial products 108 (broadly, selected crosses). In general, the pipeline 102 includes a variety of conventional processes known to those skilled in the art, as described below, used in the different phases 104, 106 to ultimately achieve the commercial products 108. As will be described in more detail hereinafter, the illustrated system 100 includes a breeding engine 112 uniquely configured, in connection with crosses data structure 114, to make and provide the selection of parents to the breeding pipeline 102, and in particular to the parent selection and crossing phase 104 thereof (thereby facilitating an improved likelihood of providing successful commercial products 108, and potentially utilizing fewer parents/crosses in phase 104 than in traditional operations).

Once the parents are selected/identified, in phase 104 of the pipeline 102, the parents are actually crossed (still in phase 104) to derive a plant (e.g., a seed) from the specified parents. Again, it should be appreciated that any convention methods of crossing plants may be employed to actually create the population of plants, once the parents have been selected as described herein. Specifically, those skilled in the art would understand that various different types of fertilization between two parents may be employed herein, often depending on the types of parents selected, to create a plant. Other manners of complex crossing schemes known in the art may further be used to create a population of plants in the selection and crossing phase 104, including, for example, 3-way crosses, 4-way crosses, 5-way crosses, etc., within and among different groups of hybrids, inbreds, heterotic designations, races, ploidy levels (e.g., haploids, diploids, doubled-haploids, triploids, polyploids, etc.), species, etc. In addition, a variety of different manners of creating plants between two plants or plant cells may also be used in connection with creating the population of crosses.

Once the population of crosses is created in phase 104 of the pipeline 102, it is directed to the testing and selection phase 106, which includes a growing space, such as, for example, a greenhouse, a nursery, a breeding plot, a field, etc. Once the plants are derived from the crosses (in phase 104), based on one or more conventional methods (as described above), the plants are planted in, or more generally subject to, the growing space in phase 106, whereupon the plants are grown. Within this phase 106, after or as part of growing, the crosses may be subjected to any number of tests. The tests are generally employed to determine which of the crosses in the population should be advanced for subsequent testing/evaluation (as part of the testing and selection phase 106) and/or which should be advanced as a commercial product 108, where such selections/advancements are made depending on various criterion including (but not limited to) resistance to certain diseases, resistance to certain pests, visual inspection, cost of goods associated with the crosses, propensity of the crosses to produce haploid offspring, propensity of the crosses to product double haploid offspring, propensity of the crosses for induction, and/or propensity of the crosses to have a number of chromosomes in at least one of their cells to be doubled.

In the testing and selection phase 106, the crosses (e.g., the resulting seeds from the parental crosses, the resulting plants from the parental crosses, etc.) are tested for the presence of at least one trait via one or more techniques known in the art of plant breeding. Such techniques may include any number of tests, trials, or analyses known to be useful for evaluating plant performance, including any phenotyping or genotyping assays known in the art. Common examples of seed phenotypes, which may be evaluated, include size, shape, surface area, volume, mass, and/or quantity of chemicals in at least one tissue of the seed, for example, anthocyanins, proteins, lipids, carbohydrates, etc. in the embryo, endosperm or other seed tissues. Where a plant (e.g., cultivated from a seed, etc.) has been selected or otherwise modified to produce a particular chemical (e.g., a pharmaceutical, a toxin, a fragrance, etc.), the seed can be assayed to quantify the desired chemical. Based on the results of such test(s), a breeder or other user may then select for advancement in the pipeline 102 those seeds or population(s) of seeds that appear to contain one or more desired traits. Examples of genetic analyses may include any form of nucleic acid detection and/or characterization, including sequencing, genotyping by sequencing, detection and characterization of sequences associated with certain alleles and/or quantitative trait loci, allele frequencies in a population of seeds, transgene, or RNA sequences in that a user is interested, etc.

In connection with such testing, tissue of the crosses (e.g., of the resulting seeds, of the resulting plants, etc.) may also be genotyped using any methods useful to breeders (as opposed to testing the entire seed or plant). Common examples include harvesting samples of embryo and/or endosperm material/tissue in a way that does not kill or otherwise prevent the seeds or plants from surviving the ordeal. For example, seed chipping may be employed to obtain seed samples from the crosses for use in determining whether a specific sequence of nucleic acid is contained within the seed and/or, potentially, within a population from which the sampled seed was derived. Any other methods of harvesting samples of tissue of the seeds for analysis can be used for the purposes of genotyping, as well as conducting genotyping assays directly on the tissue of the seeds that do not require samples of tissue to be removed. In certain embodiments, the embryo and/or endosperm remain connected to other tissue of the seeds. In certain other embodiments, the embryo and/or endosperm are separated from other tissue of the seeds (e.g., embryo rescue, embryo excision, etc.).

Moreover, the tissue of the seeds (or plants) may be accessed via one or more of a wide range of methods to genotype the crosses. Commonly used methods include, for example, using at least one molecular marker (e.g., a single-nucleotide polymorphism (SNP) marker, etc.) and/or at least one sequencing-based method (e.g., genotype by sequencing (GBS), etc.) to detect the presence of certain nucleotide sequences in the embryo or endosperm of the seeds or plants. It should be appreciated that other useful methods of detecting, quantifying, and/or comparing nucleotide sequences in plant embryo or endosperm tissue of the seeds could be employed in conjunction with the methods described herein, depending on circumstances (e.g. species of plants, number of plants to genotype, size of breeding program, etc.). In general, any genotyping method (or phenotyping method) that a user employs to aid in the process of selecting seeds or plants (or embryos, or endosperms) for advancement to a next stage in the testing and selection phase 106, and/or in the breeding pipeline 102, may be used.

With that said, it should be appreciated that the testing and selection phase 106 of the breeding pipeline 102 in the illustrated embodiment is not limited to certain or particular genotyping or phenotyping methods or technologies when assaying the crosses (and/or tissues on and/or within crosses), as any method and/or technology suitable to aid in the determination of a genotype and/or phenotype of the crosses' cells at any stage of the life cycle may be used. In one example, a plant researcher may germinate a seed from a cross and/or cultivate the plant from an embryo to some later development stage in order to complete a test useful for making selections on the plant. Conversely, in certain examples, it may be advantageous to test and select plants based on assays that can be conducted without germinating a seed or otherwise cultivating a plant sporophyte.

The testing and selection phase 106 of the breeding pipeline 102 may also include multiple iterations, as indicated by the arrows in FIG. 1, in which crosses are grown and/or testing and selections are made, and whereby the population of potential crosses is reduced. The testing performed at different parts of the testing and selection phase 106 may be modified between different ones of such iterations, to reduce the population of crosses based on any desirable criteria. What's more, further modification of the population of crosses may be completed as part of the testing and selection phase 106, where different traits are added to the crosses, such as, for example, resistance to one or more pests, diseases, etc.

Finally in the breeding pipeline 102, based on the results of the testing and selection phase 106, seeds or populations of seeds are advanced to become commercial products 108. The seeds and/or crosses are then generally bulked to provide seeds to be sold commercially and/or potentially for other further final testing of the selected seeds.

With continued reference to FIG. 1, the breeding engine 112 of the system 100 is configured, by computer-executable instructions, to select crosses to provide to the breeding pipeline 102 (specifically, to the parent selection and crossing phase 104) for use therein as described above. For example, once provided to the parent selection and crossing phase 104, the selected/identified parents (as provided by the breeding engine 112) are actually crossed (at phase 104).

In particular in the system 100, the breeding engine 112 is configured to access the crosses data structure 114 and, based on data therein, generate a population prediction score for each of the crosses in the data structure 114 (specifically, based on data in the crosses data structure 114 associated with the parents to be crossed). The breeding engine 112 is configured to then generate and/or retrieve, from the data structure 114, population prediction scores for select ones (or all) of the crosses in the population. In addition, the breeding engine 112 is configured to select (e.g., filter, etc.) a subgroup of the crosses based on a threshold associated with the population prediction scores, and to further select (e.g., filter, etc.) a pool of target crosses from the subgroup based on the relatedness of the parents within the subgroup (e.g., to help achieve a generally manageable number of potential crosses for implementation in the breeding pipeline 102, etc.).

Next, the breeding engine 112 is configured to discard (i.e., not select for advancement in the pipeline 102) parents from the pool of target crosses (and thus remove undesired crosses coming from these parents) that contain undesired traits based on a set of one or more predetermined rules and associated thresholds (as defined by the rules). Any number of rules and thresholds may be applied in connection with discarding the unwanted/undesired crosses (and, thus, their parents) (e.g., ten rules, less than ten rules, eighteen rules or less, twenty rules or less, more than twenty rules, any other number of rules, etc.). The rules and associated thresholds may be stored in the crosses data structure 114, or they may be stored separately in memory associated with the breeding engine 112. In addition, the rules and thresholds may be generated by breeders (or other users of the system 100), as desired, and/or may be based on historical data (e.g., historical data included in the data structure 114, other historical data, etc.). With that said, it should be appreciated that a variety of different rules, based on trait values for the parents, for example, may be employed by the breeding engine 112 to help improve overall quality of the crosses remaining in the system 100 after initial selection.

Table 1 illustrates five example rules and corresponding thresholds that may be used by the breeding engine 112 in connection with filtering out, or culling, parents (or crosses) from a pool of target crosses (or target parents), based on undesired phenotype traits and/or characteristics. In particular, the rules in Table 1 relate to stalk lodging (STLP), root lodging (RTLP), Goss Wilt (GW), parental similarity (SIMILARITY), and the difference between the expected relative maturity (ERM) between the two parents (i.e., dERM).

TABLE 1

| Rule | Threshold |
| --- | --- |
| STLP | 140 |
| RTLP | 140 |
| GW | 6 |
| SIMILARITY | 0.9 |
| dERM | 20 days |

After selecting the desired crosses (and parents) from the crosses data structure 114 and establishing a pool of potential crosses (and parents or origins), the breeding engine 112 is configured to then select at least one cross from the pool of remaining crosses (i.e., select two parents from the pool to cross), based on potential to produce commercial offspring as well as on populating the breeding pipeline 102 with a diverse pool of lines. Populating the breeding pipeline 102 with a diverse pool of lines may include one or more of choosing parents to cross that show resistance to several diseases, choosing parents to cross that are tested in the pipeline 102 for several years, and directing the pipeline 102 to include a desired product portfolio to meet current and/or predicted market needs. Once the selection is made, the breeding engine 112 is configured to direct the selected ones of the parents (or the selected crosses) to the breeding pipeline 102 to actually be crossed.

It should be appreciated that, throughout the breeding pipeline 102, and for multiple prior pipelines (not shown), the data related to the parents and/or the crosses of parents is compiled into the crosses data structure 114 from the breeding pipeline 102 (as indicated by the dotted lines in FIG. 1). In addition, the data structure 114 includes historical data 116 for years 1-N, for desired seeds, plants, etc. (e.g., maize in the various examples herein, etc.). As such, the data structure 114 includes data for multiple different seed parents and various example metrics, characteristics and/or traits, etc. associated therewith, as well as with the potential crosses thereof, for use by the breeding engine 112. For example, the data structure 114 may include data related to tassel skeletonization in the offspring of a particular maize inbred. Additionally, the data structure 114 may include data related to the occurrence of tolerance to root knot nematode infection in the offspring of a particular soybean or cotton plant. Similarly, the data structure 114 may include data related to other characteristics of maize, or other characteristics of other crops.

Figure 2:
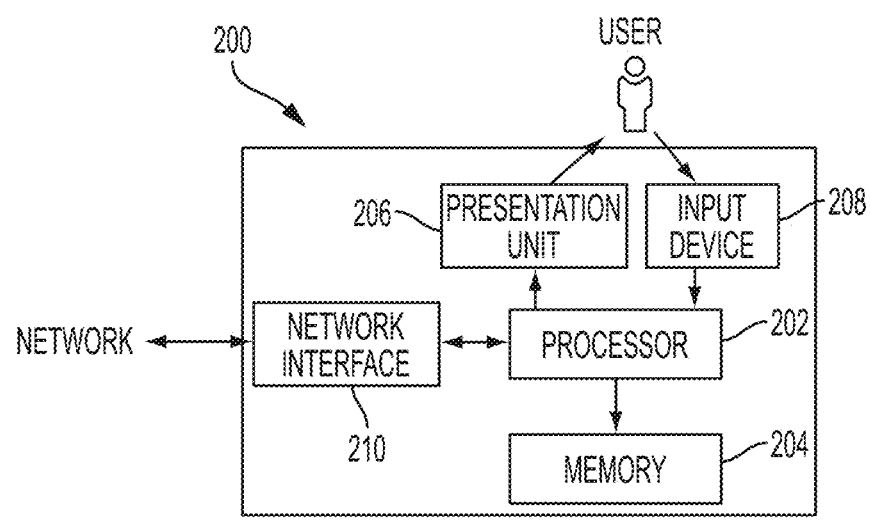
FIG. 2 is a block diagram of a computing device that may be used in the exemplary system of FIG. 1.

FIG. 2 illustrates an exemplary computing device 200 that may be used in the system 100, for example, in connection with various phases of the breeding pipeline 102, in connection with the breeding engine 112, the crosses data structure 114, etc. For example, at different parts of the breeding pipeline 102, breeders or other users interact with computing devices, consistent with computing device 200, to enter data and/or to access data in the crosses data structure 114 to support breeding decisions and/or testing completed/accomplished by such breeders or other users. Further, the breeding engine 112 includes at least one computing device consistent with computing device 200. In connection therewith, the computing device 200 may be configured, by executable instructions, to implement the various algorithms and other operations described herein. It should be appreciated that the system 100, as described herein, may include a variety of different computing devices, either consistent with computing device 200 or different from computing device 200.

The exemplary computing device 200 may include, for example, one or more servers, workstations, personal computers, laptops, tablets, smartphones, other suitable computing devices, combinations thereof, etc. In addition, the computing device 200 may include a single computing device, or it may include multiple computing devices located in close proximity or distributed over a geographic region, and coupled to one another via one or more networks. Such networks may include, without limitations, the Internet, an intranet, a private or public local area network (LAN), wide area network (WAN), mobile network, telecommunication networks, combinations thereof, or other suitable network(s), etc. In one example, the crosses data structure 114 of the system 100 includes at least one server computing device, while the breeding engine 112 includes at least one separate computing device, which is coupled to the crosses data structure 114, directly and/or by one or more LANs, etc.

With that said, the illustrated computing device 200 includes a processor 202 and a memory 204 that is coupled to (and in communication with) the processor 202. The processor 202 may include, without limitation, one or more processing units (e.g., in a multi-core configuration, etc.), including a central processing unit (CPU), a microcontroller, a reduced instruction set computer (RISC) processor, an application specific integrated circuit (ASIC), a programmable logic device (PLD), a gate array, and/or any other circuit or processor capable of the functions described herein. The above listing is exemplary only, and thus is not intended to limit in any way the definition and/or meaning of processor.

The memory 204, as described herein, is one or more devices that enable information, such as executable instructions and/or other data, to be stored and retrieved. The memory 204 may include one or more computer-readable storage media, such as, without limitation, dynamic random access memory (DRAM), static random access memory (SRAM), read only memory (ROM), erasable programmable read only memory (EPROM), solid state devices, flash drives, CD-ROMs, thumb drives, tapes, hard disks, and/or any other type of volatile or nonvolatile physical or tangible computer-readable media. The memory 204 may be configured to store, without limitation, the crosses data structure 114, parent and/or cross selection/cull rules, various thresholds as used herein, various scores as used herein, breeding decisions, data related to commercial products, and/or other types of data (and/or data structures) suitable for use as described herein, etc. In various embodiments, computer-executable instructions may be stored in the memory 204 for execution by the processor 202 to cause the processor 202 to perform one or more of the functions described herein, such that the memory 204 is a physical, tangible, and non-transitory computer-readable storage media. It should be appreciated that the memory 204 may include a variety of different memories, each implemented in one or more of the functions or processes described herein.

In the exemplary embodiment, the computing device 200 also includes a presentation unit 206 that is coupled to (and is in communication with) the processor 202. The presentation unit 206 outputs, or presents, to a user of the computing device 200 (e.g., a breeder, etc.) by, for example, displaying and/or otherwise outputting information such as, but not limited to, selected parents for use in a cross, selected crosses to advance as commercial products, and/or any other type of data. It should be further appreciated that, in some embodiments, the presentation unit 206 may comprise a display device such that various interfaces (e.g., applications (network-based or otherwise), etc.) may be displayed at computing device 200, and in particular at the display device, to display such information and data, etc. And in some examples, the computing device 200 may cause the interfaces to be displayed at a display device of another computing device, including, for example, a server hosting a website having multiple webpages, or interacting with a web application employed at the other computing device, etc. Presentation unit 206 may include, without limitation, a liquid crystal display (LCD), a light-emitting diode (LED) display, an organic LED (OLED) display, an "electronic ink"

display, combinations thereof, etc. In some embodiments, the presentation unit 206 may include multiple units.

The computing device 200 further includes an input device 208 that receives input from the user. The input device 208 is coupled to (and is in communication with) the processor 202 and may include, for example, a keyboard, a pointing device, a mouse, a stylus, a touch sensitive panel (e.g., a touch pad or a touch screen, etc.), another computing device, and/or an audio input device. Further, in some exemplary embodiments, a touch screen, such as that included in a tablet or similar device, may perform as both the presentation unit 206 and the input device 208. In at least one exemplary embodiment, the presentation unit 206 and the input device 208 may be omitted.

In addition, the illustrated computing device 200 includes a network interface 210 coupled to (and in communication with) the processor 202 (and, in some embodiments, to the memory 204 as well). The network interface 210 may include, without limitation, a wired network adapter, a wireless network adapter, a telecommunications adapter, or other device capable of communicating to one or more different networks. In at least one embodiment, the network interface 210 is employed to receive inputs to the computing device 200. For example, the network interface 210 may be coupled to (and in communication with) in-field data collection devices, such as those described in PCT Application No. PCT/US2015/045301, titled "Apparatus And Methods For In-Field Data Collection And Sampling," filed Aug. 14, 2015, and corresponding U.S. Provisional Application No. 62/037,968, filed Aug. 15, 2014 (the disclosure of each being incorporated by reference herein in their entirety), in order to collect data for use as described herein. In some exemplary embodiments, the computing device 200 includes the processor 202 and one or more network interfaces incorporated into or with the processor 202.

It should be appreciated that the breeding engine 112 may be configured to provide (e.g., generate and cause to be displayed at a computing device of a breeder) and/or respond to a user interface, through which a breeder (broadly, a user) is able to make selections and provide inputs regarding parents and crosses. The user interface may be provided directly at a computing device (e.g., computing device 200, etc.) of the breeder, in which the breeding engine 112 is employed, or via one or more network-based applications through which a remote user (again, potentially a breeder) may be able to interact with the breeding engine 112 as described herein.

FIGS. 3A-3F illustrate an exemplary excerpt 300, which forms part of the crosses data structure 114 of the system 100. As such, the data contained in the excerpt 300 is stored in memory (e.g., memory 204, etc.), and accessed by the breeding engine 112 to perform the operations as described herein. The illustrated excerpt 300 generally includes a table identifying multiple different crosses for maize, along with the parents P1, P2 of each of the different crosses (FIG. 3A), and various example metrics, characteristics and/or traits associated with the crosses and/or the parents P1, P2 (FIGS. 3A-3F). As shown in FIGS. 3A and 3B (columns D-O), the excerpt 300 includes example metrics, characteristics and/or traits such as, and without limitation, linear unbiased predictors of selection indexes of parents (P1_SELIN_blup, P2_SELIN_blup), best linear unbiased predictors of yield of the parents (P1_YLD_BE_blup, P2_YLD_BE_blup), moisture content of the parents (P1_MST_blup, P2_MST_blup), selection test mean of the parents (P1_SELTM_blup, P2_SELTM_blup), test weights of the parents (P1_TWT_blup, P2_TWT_blup), and root lodging of the parents (P1_RTLP_blup, P2_RTLP_blup). This data is generally obtained from annual field trials. In addition, FIG. 3B (columns P-S) illustrates various metrics that may be used herein, such as probability that a parent tested in a stage can advance to a next stage (P1_AVG_SCORE_PS1, P2_AVG_SCORE_PS1, P1_PR_ADV, P2_PR_ADV). These metrics are obtained from machine learning models that are trained to predict a probability of the parent in the identified cross advancing each stage of the breeding pipeline.

It should be appreciated that the excerpt 300 is exemplary in nature and is provided herein for purposes of illustration only. Those skilled in the art will readily understand that additional and/or different data may be included related to various metrics, characteristics and/or traits of the crosses and/or their parents P1, P2. Further, the excerpt 300 may include additional and/or different metrics, for example, scores, ranges, thresholds, and/or other mechanisms, etc., by which the crosses may be identified and/or (un)selected, in the systems and methods described herein.

Figure 4:
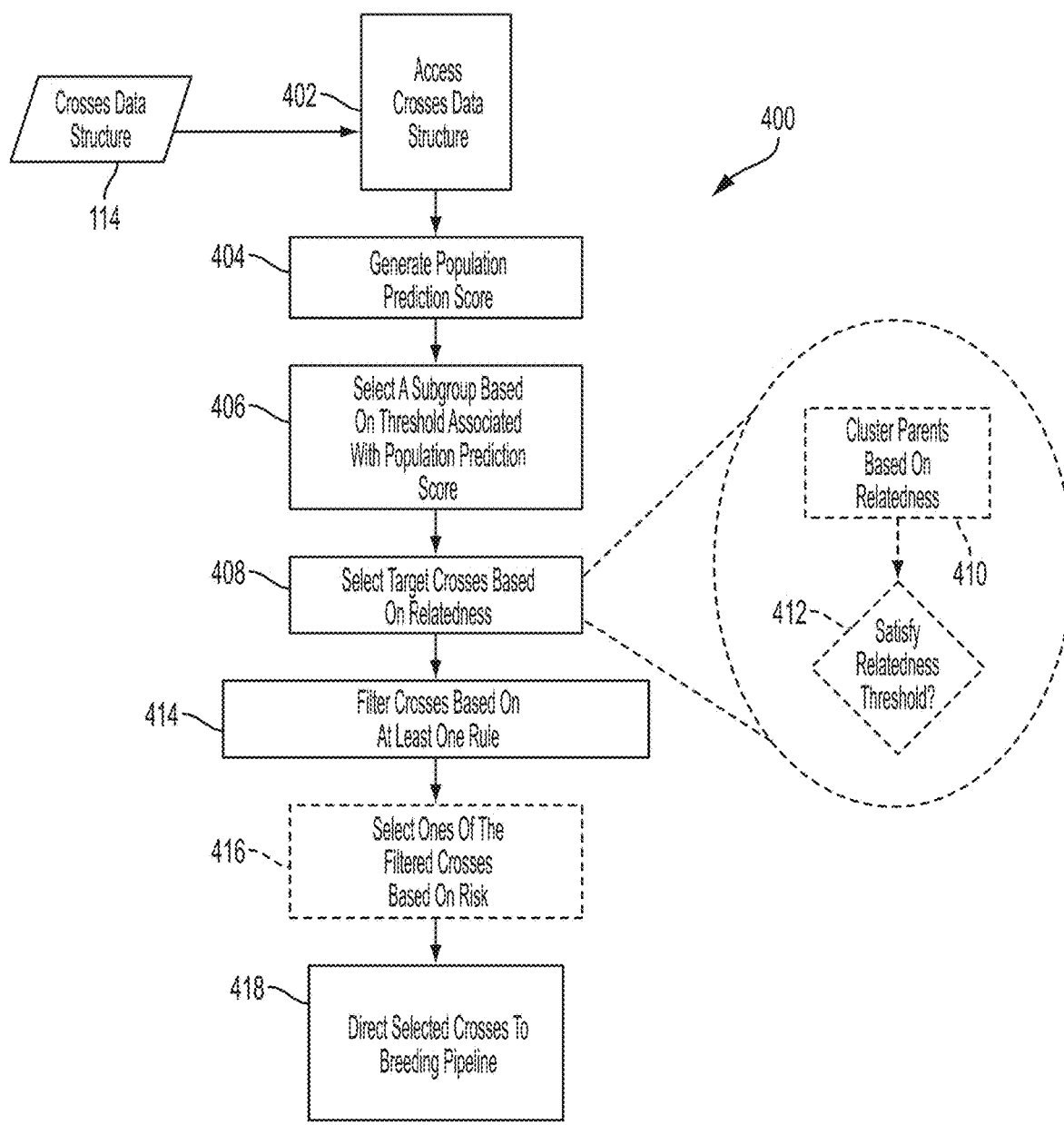
FIG. 4 is an exemplary method, suitable for use with the system of FIG. 1, for identifying plant crosses for use in plant breeding.

FIG. 4 illustrates an exemplary method 400 of selecting crosses of certain parents in a plant breeding process. The exemplary method 400 is described herein in connection with the system 100, and may be implemented in the breeding engine 112 of the system 100. Further, for purposes of illustration, the exemplary method 400 is also described with reference to the computing device 200 of FIG. 2 and the excerpt 300 of FIGS. 3A-3F from the crosses data structure 114 of the system 100. However, it should be appreciated that the method 400, or other methods described herein, are not limited to the system 100, the computing device 200, or the excerpt 300. And, conversely, the systems, data structures, and the computing devices described herein are not limited to the exemplary method 400.

To begin, a breeder (or other user) initially identifies a desired plant type for breeding, potentially consistent with one or more desired characteristics and/or traits to be advanced, or a desired performance. For example, for a region in the central, southern United States, a breeder whose objective is maize may select to breed drought resistant maize that is not susceptible to Goss Wilt disease, and that also meets a predefined diversity criterion (e.g., to help maintain integrity of the breeding program, etc.). Once identified, the breeder provides one or more inputs to the breeding engine 112 (e.g., via computing device 200 using a network-based application or other application, etc.) consistent with the desired plant type and/or desired characteristics and/or traits. In the example above, the inputs that the breeder provides may include an input identifying maize as the desired plant along with three weight inputs that define the relative importance of the drought resistance characteristic, the Goss Wilt resistance characteristic, and the diversity requirement.

In turn in the method 400, upon receiving the desired inputs from the breeder, the breeding engine 112 accesses, at 402, the crosses data structure 114 and initially identifies potential parents for breeding (based on the inputs), thereby resulting in identification of a set of potential crosses. In connection with such identification, the parents (and crosses) within the data structure 114 may be limited in one or more high-level manners consistent with one or more user inputs from the breeder, including, for example, selection of parents (and crosses) consistent with the particular plant type indicated (e.g., maize, etc.), the predicted performance (e.g., yield, etc.), the region of intended growing (e.g., central, southern United States; etc.), growing environments (e.g., arid, etc.), market needs in the intended region of growing, certain genotype or phenotype characteristics (e.g., tolerances to disease and/or stress such as drought, traits that make crosses cost-effective to commercialize and/or produce on an industrial scale, etc.), the desired product portfolio in the desired region of breeding, or any other trait, characteristic, or outcome potentially input (or otherwise desired) by the breeder.

Upon accessing the data structure 114, and initially identifying potential parents/crosses based on the breeder's preliminary inputs, the breeding engine 112 generates, at 404, a population prediction score for selected crosses involving the selected potential parents. The population prediction score may be generated for the identified crosses, by the breeding engine 112, each time the breeding engine 112 selects or identifies them for possible use in the plant breeding pipeline 102 (consistent with FIG. 4). Or, the population prediction score may alternatively be generated intermittently (e.g., periodically, or at one or more regular or irregular intervals, etc.), by the breeding engine 112 (e.g., as an update based on new data provided to the crosses data structure 114, etc.), and stored in the crosses data structure 114 to limit regeneration upon subsequent use of the score by the breeding engine 112.

It should be understood that the population prediction score is generally a prediction of commercial success for each of the selected crosses. Commercial success may be defined by any desired metric of performance. Common examples of commercial success for a cross include being selected for advancement to some point in the breeding system 100, whereby the cross is "coded" for commercialization and/or the cross is actually released as a commercial product. Additionally, or alternatively, commercial success may represent a cross's performance as a commercial product (e.g., a certain number of units of the product were sold on the market, a number of years the cross is in the market, etc.).

In connection with determining a particular population prediction score, the breeding engine 112 employs one or more different supervised, unsupervised, or semi-supervised algorithms/models such as, but not limited to, random forest, support vector machine, logistic regression, tree based algorithms, naïve Bayes, linear/logistic regression, deep learning, nearest neighbor methods, Gaussian process regression, and/or various forms of recommendation systems algorithms (See "Machine learning: a probabilistic perspective" by Kevin P. Murphy (MIT press, 2012), which is incorporated herein by reference in its entirety, to determine the population prediction score for each of the selected crosses (and thereby estimate commercial success). The scores generated by various methods can then be combined using methods such as, but not limited to, bagging and boosting, blending, ensemble methods, Bayesian model combination (BMC), simple averaging, weighted averaging, etc. See, e.g., "Ensemble Methods in Data Mining: Improving Accuracy Through Combining Predictions," Giovanni Seni and John Elder, 2010 (Morgan and Claypool Publishers); "Popular ensemble methods: An empirical study," Opitz & Maclin (1999), *Journal of Artificial Intelligence Research* 11: 169-98; and "Ensemble-based classifiers," Rokach (2010), *Artificial Intelligence Review* 33 (1-2): 1-39 (each of which is incorporated herein by reference it its entirety).

As an example, the breeding engine 112 may use a variation of BMC represented by Equation (1) to generate population prediction scores for potential crosses. The score, then, includes a weighting applied to each of the classifiers/features used in Equation (1), and the weights, in some embodiments, reflect some aspect of the data characterizing the parents and/or their offspring. For example, Equation (1) may be constructed using historical data associated with the parents of the potential crosses in the crosses data structure 114, and may be accessed by the breeding engine 112 from within the data structure 114 as needed.

$$p(s_i|x_i,D) = \sum_{m=1}^{M} p(s_i|x_i,m,D)p(m|D) \quad (1)$$

In Equation (1), $s_i$ represents success (or failure) of the new crosses being predicted herein. As such, $p(s_i|x_i, D)$ generally represents probability that the cross will be a success. Further, $x_i$ corresponds to the features of the given cross that are being predicted (see further discussion below regarding such features), D refers to historical data being used to train the given models (and which contains both features and advancement information of the cross in the associated pipeline), and m refers to the classifier model itself.

In connection with the excerpt 300 illustrated in FIGS. 3A-3F from the crosses data structure 114, the breeding engine 112 may employ, for each of the identified crosses coming from parents P1, P2, the following features (among others) in generating the population prediction scores for the potential crosses: BLUP (best linear unbiased prediction) general combining ability (P1_BlupModel, P2_BlupModel) in columns Y-Z of FIG. 3C, marker based genetic similarity (Similarity) in column T of FIG. 3B, and performance in the pre-commercial pipeline (columns P-S of FIG. 3B) and some form of genetic data (e.g., marker data or haplotype data). The resulting population prediction scores, for each of the crosses, are then included in the excerpt 300 in columns X-Z of FIG. 3C and in columns II-MM of FIG. 3D. A final prediction score (i.e., "advScore") (computed using Equation (1)) is included in column NN of FIG. 3D. This final prediction score generally combines each of the intermediate population prediction scores. And, the predicted advancement probability for the parents, P1, P2, are included in columns R-S of FIG. 3B.

It should be appreciated that prior to reliance on any particular method or combination of methods, the breeding engine 112 may evaluate performance of the method(s) and select, if necessary, the one that provides best performance for a given crop and/or a given region, for example. In order to evaluate the performance of the methods and/or models, historical data may be collected and then partitioned into training and test sets for each of the methods. Models are then built, based on the different methods, using the training data to predict the commercial success using several features for various traits, and using the historical advancement/success of the parents in the breeding pipeline 102. Once the models are built, the commercial success of the test data is predicted through the models and compared to the actual commercial success for the crosses, to determine the accuracy of the models (e.g., for each of the different methods, etc.).

With reference again to FIG. 4, the breeding engine 112 next selects, at 406, a sub-group of the crosses, based on a threshold associated with the population prediction scores. For example, a threshold of the top 40% may be employed, which is determined from historical data to capture 80% of commercial products in prior years and specific to the geographic region for the commercial products. As such, the parents with the top 40% population prediction scores from the population may be selected. The 40% threshold may be different in other embodiments, for example, to adjust a number of potential crosses in the subgroup while maintaining a desired number of commercially successful crosses (when verified against historical data), etc. In various examples, other thresholds may include, without limitation, 10%, 15%, 20%, 25%, 31%, etc., which may correspond to capturing 60%, 70%, 74%, etc. of the commercially successful crosses, historically. It should be appreciated that other thresholds may be selected (by the breeder) based on a variety of other factors including, for example, performance of an algorithm used, a confidence in the algorithm, a number of potential crosses at start, etc.

After selection of the sub-group, the breeding engine 112 selects target crosses from the sub-group, at 408, based on relatedness of the parents of the crosses within the sub-group. In this exemplary embodiment, the relatedness of the parents is employed, by the breeding engine 112, to inhibit final selected crosses from being too closely related, i.e., to promote genetic diversity and/or to avoid risk of choosing a same parent among a substantial number of the final selected crosses. Specifically, for example, when a parent is preferred for one or more reasons (e.g., based on probability prediction score, etc.), the parent may be selected for multiple of the crosses in the sub-group. However, if the parent or its parents (broadly, the parental line) is/are flawed, the crosses including that parent may be disqualified from being a commercial product 108 in the system 100. By promoting diversity of the parents as described herein, the method 400 limits the potential impact of certain flawed parental lines in the breeding pipeline 102.

In particular in the method 400, in connection with selecting the target crosses, the breeding engine 112 optionally (as indicated by the dotted lines in FIG. 4) clusters the parents, at 410, based on relatedness of the parents, through use of similarity markers. In so doing, for example, the breeding engine 112 characterizes a distance between two parents, where less similarity exists for two parents that are separated by a greater distance. The similarity markers are typically computed apart from the method 400 using raw marker data for the parents (as included in data structure 114, for example), with a simple matching coefficient as the similarity measure. Specifically, in this exemplary embodiment, after fingerprinting two parents, corresponding markers in each parent may be compared, and the number of locations where they are similar, divided by the total number of markers, may provide a similarity coefficient (or marker) between two parents. In connection with the excerpt 300 of FIGS. 3A-3F, for example, the similarity coefficients or markers for the potential crosses identified therein are shown in column T (SIMILARITY) of FIG. 3B.

As an example, the breeding engine 112 may determine a distance metric for each potential cross, based on the relatedness of the parents, through use of Equations (2) and (3).

$$l_{ij} := 1 - e^{\frac{(1-s_{ij})^2}{a^2}}, i \neq j \quad (2)$$

$$l_{ii} := -\sum_{j, j \neq i} l_{ij} \quad (3)$$

In Equations (2) and (3), $s_{ij}$ is the similarity between $i^{th}$ and $j^{th}$ parents, and $l_{ij}$ is the $ij^{th}$ cross entry of the Laplacian matrix L. As such, in this exemplary embodiment, the breeding engine 112 employs spectral clustering, followed by Eigen Analysis, to determine/estimate a number of clusters, and then K-Means approach to cluster the parents. It should be understood, however, that a variety of other known clustering techniques may alternatively be used. The breeding engine 112 utilizes the Eigen Analysis to estimate the number of clusters in an unsupervised manner.

Then, once a desired number of clusters are determined, a dimensionality reduction is performed, by the breeding engine 112, by projecting the Laplacian matrix L onto the dominant Eigen modes, for example, via Equations (4) and (5) below. In Equation (4), L is the Laplacian matrix, created from the similarity distance $s_{ij}$, and $\hat{L}$ is the normalized Laplacian that is normalized by a diagonal matrix D. Eigen analysis of $\hat{L}$ provides the number of clusters. In Equation (5), the normalized Laplacian matrix is decomposed using a singular value decomposition. The matrix, $\Sigma$, contains the Eigen values that capture the number of the clusters of the data sets according to spectral clustering. As described above, the breeding engine 112 then clusters the parents using a K-Means algorithm. Because the K-Means algorithm is a stochastic or random clustering mechanism, the breeding engine 112 may cluster the parents in multiple different realizations of the K-Means algorithm, selecting the maximum, or higher, inter cluster distance. While spectral clustering is used herein, it should be appreciated that other clustering algorithms may be employed, at 410, including, for example, Hierarchical Clustering, Bayesian Clustering, C-means Clustering etc.

$$\hat{L} = D^{-\frac{1}{2}} L D^{-\frac{1}{2}} \quad (4)$$

$$\hat{L} = U \sum U^T \quad (5)$$

Figure 5:
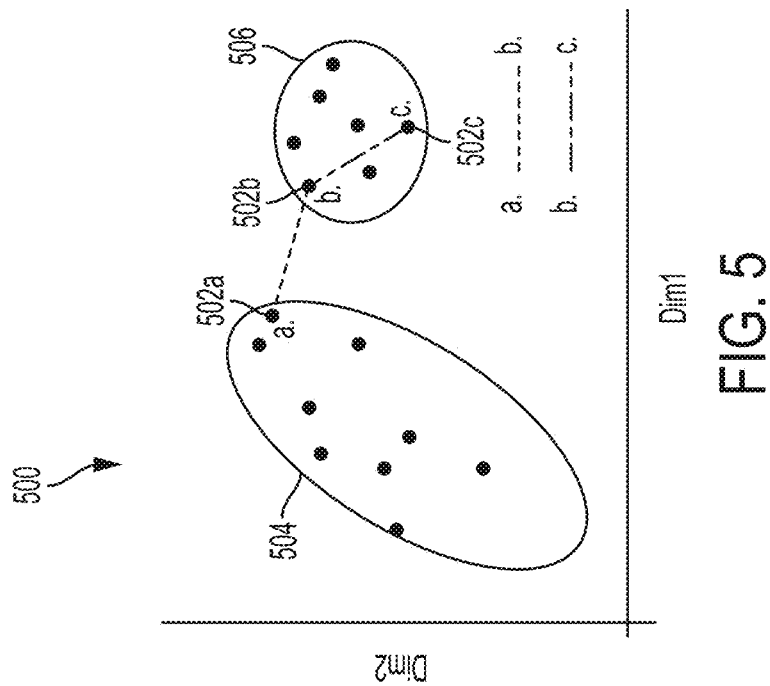
FIG. 5 is a graphical representation of clustering of parents for potential crosses.

After the clusters are formed, by the breeding engine 112, the potential crosses are classified in generic clusters depending on the clusters to which its parents belong. For each cross of parents, the breeding engine 112 computes a performance score, which is based on commercial advancement of the parents and the data collected from commercial activity, testing, etc. of the parents. In connection with the excerpt 300 of FIGS. 3A-3F, for example, the cluster performance scores for the crosses (i.e., progenyClusterScore, Cluster_Scores) are provided in columns VV-WW of FIG. 3E. In addition, an example clustering of parents for potential crosses is illustrated in FIG. 5 (corresponding to a hypothetical two dimensional space resulting from the dimensional reduction described above), where each parent is illustrated as a dot, including, specifically, parents 502*a-c*. The parents are clustered into two distinct clusters 504, 506. In this example clustering, the performance score for the cross between parents 502*a*, 502*b*, for example, may be higher than the performance score for the cross between parents 502*b*, 502*c*, because they are part of different clusters and/or because 502*c* has more advancements than 502*a*.

With reference again to FIG. 4, after clustering the parents, the breeding engine 112 then, again optionally (as indicated by the dotted lines), selects the target crosses, based on whether or not the crosses (particularly their parents) satisfy a relatedness threshold, at 412. In particular, the breeding engine 112 filters the crosses based on the relatedness threshold, which is derived from a percentage of parents of the crosses belonging to individual clusters. The number of crosses to be selected, based on parents from each cluster, for example, is proportional to the size of the genetic cluster and the score of the cluster.

Specifically, for example, in this embodiment the breeding engine 112 utilizes progeny cluster scores (the cluster scores computed using the data from the progeny produced from the given cluster), for example, column VV in excerpt 300, and cluster scores (the cluster scores computed using the data from the parents from a given cluster), for example, column WW in the excerpt 300, to filter ones of the potential crosses based on relatedness. Each of the progeny cluster scores and the cluster scores, in this embodiment, are normalized, to provide the same scale, and then combined by the breeding engine 112 in one or more manners such as, for example, addition, multiplication, etc. The cluster scores are then used to determine whether the cross will be selected at 408 (as described more below), and thereby retained in the population of potential crosses to proceed to operation 414 described below. In particular, in this exemplary embodiment, a number of crosses selected from each cluster may be proportional to the cluster score and/or size of the cluster. After determining the number of crosses to be selected from each cluster, the parents are sorted within the cluster according to a performance metric (for example, "perfMetric" in column TT in excerpt 300) and the top crosses are selected (e.g., above the number of crosses "threshold," etc.). Example pass/fail results are shown in the excerpt 300 in FIG. 3E in column XX (PASS_CLUSTER_FILTERING). Here, nine of the potential crosses include a "TRUE" notation, and are selected and thereby retained, while the other four of the potential crosses include a "FALSE" notation and are excluded. In this example, it is noted that the cross identified as L2/L1434 fails (i.e., the cross includes a "FALSE" notation in column XX of FIG. 3E) while the cross identified as L3/L1434 passes (i.e., the cross includes a "TRUE" notation in column XX of in FIG. 3E), even though both have the same cluster scores, based on the number of crosses selected and the relative perfMetric scores (column TT in excerpt 300).

It should be appreciated that an even distribution of crosses in the clusters may or may not occur, as a different number of crosses can be selected from each, or some, of the clusters. For example, more crosses may be selected which include parents from clusters with higher cluster scores. In any case, once it is determined how many crosses to select from each cluster, a corresponding number of top crosses are selected from each of the clusters and sorted according to performance scores (e.g., the perfMetric score shown in column TT in excerpt 300, etc.). For example, in connection with the excerpt 300, after obtaining the cluster scores shown in columns VV-WW, the breeding engine 112 sorts the crosses within each genetic cluster according to the perfMetric score in column TT. The sorted clusters are shown in column W of the excerpt 300 (ORIGIN_CLUSTER_INDEX). Here, example clusters include M_1_3, M_3_3 (Male Clusters), and F_2_2, F_1_2 (Female Clusters). Within each of these clusters, the crosses are sorted by the breeding engine 112, and a number of the crosses are selected (e.g., based on relative ranking, etc.). As previously indicated, the number of crosses to be selected within each of the clusters may be, generally, linearly proportional to the size of the cluster and the average cluster scores. In general, it is contemplated that the clusters with higher average scores will contain higher genetic value.

Next in the method 400, the breeding engine 112 filters the target crosses based on at least one rule, at 414, accessed from or retrieved from a rule data structure, for example, associated with the crosses data structure 114, etc. The rules may include any desired rules such as, for example, the rules described above in connection with Table 1, etc. In general, the rules are generally standardized and are built based on the characteristics and/or traits of the parents, crosses, and/or their lines, and may be any criterion the breeder desires to use, including any genotype, phenotype, or any other trait or characteristic that can be used to describe and/or distinguish a plant or commercial crop product and/or their performance. Common example bases for rules include stalk strength, root strength, yield, disease tolerance, stress tolerance, cost of developing into a commercial product, cost of goods, test weight, plant height, ear height, as well as those criterion and/or technologies described in other sections herein for distinguishing tissues and/or performances.

In connection with the excerpt 300 of FIGS. 3A-3F, for example, the breeding engine 112 may select parents (or potential crosses) (e.g., in connection with operation 414 in method 400, etc.), based on three rules: parent dropped, root strength, and stalk strength. In certain embodiments, when a drop rule is applied, crosses with parents satisfying the rule will advance to subsequent operations of method 400, while the remaining will be removed, or unselected (or vice-versa). In certain embodiments, when a root strength rule is applied, for example, the breeding engine 112 will select only those crosses (and their parents) whose root strength scores are higher (or lower) than a threshold set by the breeder or other user; those crosses (and their parents) whose root strength scores do not meet or exceed the threshold (or vice-versa) are not selected for advancement onto commercialization. In certain other embodiments, this process can run through several iterations, until each cross has been evaluated against all the rules and/or performance thresholds and/or criteria that the breeder wishes to use to select the preferred crosses for advancement. With reference to FIG. 3E, column YY (PASS_RULE_FILTER) in the excerpt 300 represents the cumulative/iterative results of the breeding engine 112 (e.g., in connection with operation 414 of method 400, etc.) applying various rules (e.g., the three rules identified above, etc.) to an example data set for parents P1, P2. In particular, parents L_592, L_349, L_1460, and L_638, as designated in columns A, B, are indicated, in column YY, as satisfying all the thresholds set by the breeder (while all of the other parents/crosses do not).

At 416 in the method 400, the breeding engine 112 optionally (as indicated by the dotted lines in FIG. 4) selects ones of the selected filtered crosses based on certain risks associated therewith. As an example, the breeding engine 112 may use a quadratic algorithm such as that represented by Equation (6) to find a set of desired parents to use, taking into account the risks and diversity associated with the selected set of parents.

$$x_{OPT} = \text{argmax } \lambda_{perf}(c^T x + x^T P x) - \frac{1}{2}(\lambda_{risk} x^T R x + \lambda_{div} x^T S x) \quad (6)$$

subject to $\sum x_i = 1, x_i \geq 0 \forall i$ and $$\sum_{x_i \in F} x_i \geq 0.4 \text{ and } \sum_{x_i \in M} x_i \geq 0.4$$

Figure 6:
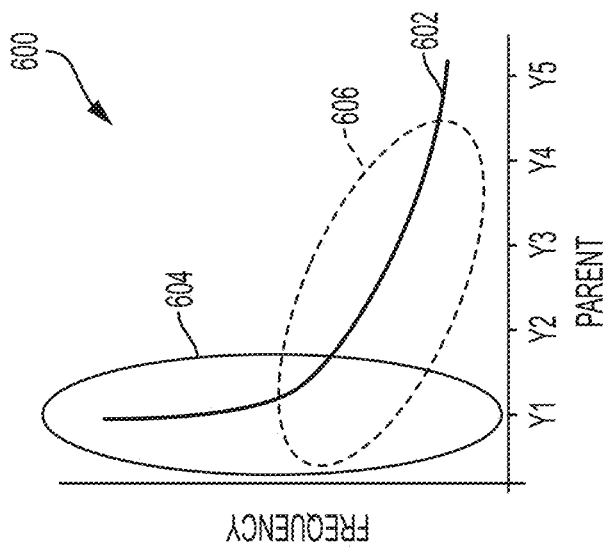
FIG. 6 is another graphical representation of an exemplary distribution of parental usage in certain breeding populations.

Equation (6) solves for an optimal set of parent distributions, which would be captured in the decision variable x. In Equation (6), $x_i$ represents a proportion of the $i^{th}$ parent; $c_i$ represents performance of the $i^{th}$ parent; $p_{ij}$ represents a performance index of the cross between the $i^{th}$ parent and $j^{th}$ parent; $r_{ij}$ represents a risk index of the cross between the $i^{th}$ parent and $j^{th}$ parent; and $s_{ij}$ represents similarity between the $i^{th}$ parent and $j^{th}$ parent. In addition, $\lambda_{perf}$, $\lambda_{risk}$, and $\lambda_{div}$ are the weights for performance, risk, and diversity, respectively. In Equation (6), the $c^T x + x^T P x$ terms denote the performance; $x^T R x$ is the risk (R is a matrix representation of the terms $r_{ij}$ (the risk value computed in column VV in the excerpt 300, for example, between lines) and computed for each of the pair of possible parent combinations or crosses, as indicated below); and $x^T S x$ is the similarity. The breeding engine 112 thus attempts to improve (if not maximize) performance, limit (if not minimize) risk, and limit (if not minimize) similarity, through Equation (6). The constraints in Equation (6) impose that x is a probability distribution, and balance the distribution by gender. FIG. 6, then, shows a graphical representation 600 of the parental usage 602 in an example system (where the selection 604 identifies parents more frequently used in early years, and the selection 606 identifies parents less frequently used in later years). By solving the quadratic program described in Equation (6), the breeding engine 112 generally inhibits use of parents with similar genetic backgrounds, thereby accounting for (and, potentially, improving) population diversity.

Figure 7:
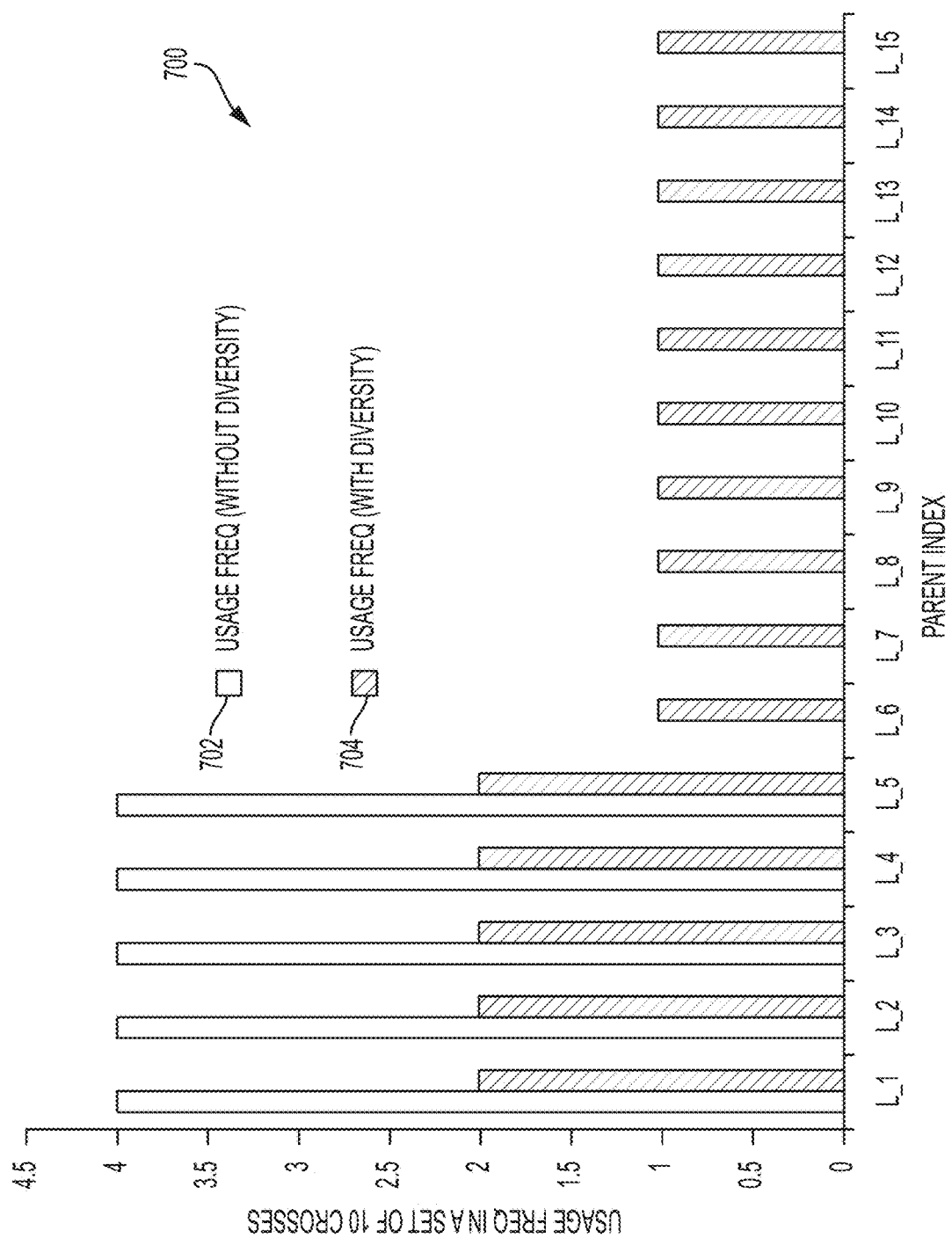
FIG. 7 is a graphical representation of a hypothetical distribution of parental usage in breeding populations in certain breeding systems.

FIG. 7 is a hypothetical graphical representation 700 of a distribution of parental usage in a breeding system, which provides an illustration of the effect of considering the diversity term in Equation (6) (i.e. $\lambda_{div} x^T Sx$), as compared to not incorporating and/or considering the term. In particular, as shown, a first set of bars 702 shows a hypothetical distribution of parents for a population of crosses based on conventional methods (i.e., in the absence of consideration of diversity), while a second set of bars 704 shows a hypothetical redistribution of the parents for a population of crosses as potentially achieved by the systems and methods herein (i.e., a hypothetical consideration of diversity). It should be understood, however, that the representation of FIG. 7 is merely provided for purposes of illustration and should not be consider a limitation of the disclosure herein or an indication of a required and/or consistent impact of the methods herein relative to conventional methods.

Referring again to FIG. 4, in connection with filtering for risks, at 416, for example, using Equation (6) to solve for parent distributions, the breeding engine 112 may, optionally, optimize (broadly, filter) the population of crosses by determining whether the parents, and/or the crosses, are associated with certain particular risks. In one example, the breeding engine 112 may determine a particular risk associated with a cross as a product of the risk of the parents, i.e., $r_{ij}=r_i r_j$. Here, the particular risks of interest for each individual parent (or of the parental line) include five risks that may be modeled, as represented by Equations (7)-(11) below, by fitting an exponential curve parameterized by the age of the parental line, the number of times the parental line is tested, and the standard deviation of the root and stalk lodging (all, broadly, risks). In particular, Equation (7) represents a risk based on age (e.g., relatively older lines would be associated with generally less risk given their longevity in the breeding pipeline 102, etc.) (reliant on columns AA and BB from excerpt 300); Equation (8) represents a risk based on number of times a hybrid is tested (e.g., the risk of using certain parental lines based on a number of times the lines have been subjected to testing in the breeding pipeline 102, etc.) (reliant on column EE from excerpt 300, which in turn is the sum of columns CC and DD (which are the numbers of tested hybrids for the parents)); Equation (9) represents a risk based on using lines with a higher root lodging (reliant on column FF from excerpt 300); Equation (10) represents a risk based on using lines with a higher stalk lodging (reliant on Column GG from excerpt 300); and Equation (11) represents a risk based on Goss Wilt susceptibility (reliant on Column HH from excerpt 300).

$$r_{age} = e^{-\alpha age} \quad (7)$$

$$r_N = e^{-\beta N_{test}} \quad (8)$$

$$r_{RTLP} = \frac{1}{1 + e^{-\alpha_1(RTLP-\beta_1)}} \quad (9)$$

$$r_{STLP} = \frac{1}{1 + e^{-\alpha_2(STLP-\beta_2)}} \quad (10)$$

$$r_{GW} = \frac{1}{1 + e^{-\alpha_3(GW-\beta_3)}} \quad (11)$$

It should be understood, however, that risks corresponding to crosses can be computed using other methods and/or other features, for example, depending on the type of the plant and the data available.

Historical data is employed to determine the various parameters of Equations (7)-(11) (i.e., $\alpha_1, \alpha_2, \alpha_3, \beta_1, \beta_2, \beta_3$). It should be appreciated, however, that risk may be accounted for via a variety of different methods known to those skilled in the art, and used herein as desired. In addition, while Equations (7)-(11) are generally directed toward risks associated with maize, it should be appreciated that risk for other plants may be account for as desired (e.g., via other methods, etc.).

Table 2 illustrates hypothetical average risk values for parents in connection with age, a number of times tested, root lodging, stalk lodging, and Goss Wilt. In particular, Table 2 illustrates how various attributes may be influenced by accounting for risk. The first column in Table 2 identifies various attributes. The second column illustrates the average risk values, for the given particular attribute, with modeling, as calculated using Equations (7)-(11). And, the third column illustrates the average risk values as calculated without modeling. Specifically, for example, the risk values for the average yield BLUP of the parents selected in Table 2 may be better when the above modeling was not applied; as shown, the risk values for root lodging, stalk lodging and Goss Wilt are better when the modeling was not applied. However, risk values for age and number of times tested for the parents selected based on the above modeling indicates that the parents have been tested more often and have spent a longer time in a corresponding breeding pipeline of the system. Thus, in this hypothetical application, the selected parents, via modeling, may have some lower average risk scores for certain attributes, but are selected nevertheless because of their demonstrated history of being selected and used in the breeding pipeline, thereby potentially reducing the overall risk associated with using them.

TABLE 2

| Attribute | Average Risk Value with Modeling | Average Risk Value without Modeling |
|---|---|---|
| Age (Years) | 2.5 | 0.5 |
| Number of times tested | 12 | 4 |
| Root Lodging BLUP | 80 | 125 |
| Stalk Lodging BLUP | 85 | 120 |
| Goss Wilt BLUP | 5 | 7 |

As shown, the risk computation takes into account the several attributes associated with crosses (e.g., age, a number of times tested, root lodging, stalk lodging, and Goss Wilt in Table 2; standability; pathological characteristics; etc.). In so doing, the risk computation, in this exemplary embodiment, helps to avoid certain attributes, with undesired risk values, heavily impacting the use of certain parents in final selections for crosses, as compared to other attributes, due to, for example, less testing of the attributes (such that the attributes may be inflated for new parental lines), etc. In Table 2, for example, the "Average Risk Value with Modeling" shows the possible values of the attributes if the risk modeling is included in Equation (6), and the "Average Risk Value without Modeling" shows the possible values if the risk modeling is omitted. The two scenarios provide a demonstration that, in the absences of risk modeling, while attempting to increase and/or maximize performance (such as for Root Lodging, Stalk Lodging, and Goss Wilt), the selected population may fail to reach desired values for several attributes like age of the parents and a number of times the parents are tested, etc. The risk computation described herein thus inhibits the selection of crosses having undesirable values for such attributes, despite potentially having high yield characteristics, for example.

Then, once the risk of the parents from individual factors is determined, for example, using Equations (7)-(11), the overall risk for each parent may be combined into a single value, using Equation (12). The risk associated with making a cross, based on the parents, is then calculated as a product of the risk of the individual parents, or $r_{ij}=r_i r_j$, where, $r_i$ and $r_j$ are calculated from Equation (12). And, the cross level risk $r_{ij}$ is then used to construct a cross level risk matrix, for example, matrix R in Equation (6), to thereby facilitate completion of operation 416.

$$r = r_{age} + r_N + r_{RTLP} + r_{STLP} + r_{GW} \quad (12)$$

Further in the method 400, in connection with operation 416, the breeding engine 112 employs Equation (13) to determine which set of crosses should be selected using the parents that were obtained through Equation (6). In Equation (13), $\lambda$ is the weight for diversity, $\mathbb{S}^\dagger$ is the incidence matrix from crosses to the parents (including 0's and 1's), $x_{opt}$ is the parent distribution calculated from Equation (6), c is the population prediction score that the breeding engine 112 computes employing Equation (1) (or other method described herein used to determine a performance index of crosses, and which relies on the BLUP of their traits, the number of commercial products in which the parents have been used, the similarity between the parents, marker data of the parents, and the scores assigned to the parental lines by the models that predicts the probability of the parents advancing through the breeding pipeline), and z is the origin selection decision vector.

$$z_{OPT} = \operatorname{argmax} c^T z - \lambda \left\| \frac{1}{n} \mathbb{S}^\dagger - x_{opt} \right\|_{\ell 1} \quad (13)$$

subject to $z^T 1 = N$ $z \in \{0, 1\}^N$ $P_{Min}^{RM} \leq S_{RM} z \leq P_{Max}^{RM}$ $P_{Min}^{GENDER} \leq S_{GENDER} z \leq P_{Max}^{GENDER}$ $P_{Min}^{Trait} \leq S_{Trait} z \leq P_{Max}^{Trait}$ The matrix $S_{RM}$ maps the origins to the Relative Maturity (RM) groups, and as a consequence, $S_{RM} z$ is the projection of usage of parents from different relative maturities. The vectors $P^{RM}_{Max}$ and $P^{RM}_{Min}$ restrict the minimum and maximum parent usage from various RM groupings. The constraint, containing the matrix $S_{GENDER}$ and vectors $P^{GENDER}_{Min}$ and $P^{GENDER}_{Max}$ maintain similar balance for gender or heterotic groups, and the $S_{Trait}$, $P^{Trait}_{Max}$, and $P^{Trait}_{Min}$ assist in maintaining various desired portfolios of traits. In view of the above, it should be appreciated that other constraints relating to frequency of a certain QTL or traits, and the desired product portfolio, may also (or alternatively) be included in a similar manner, for example, by constructing appropriate projection matrices.

In certain embodiments, an iterative process of the above operations may be applied to successively narrow down the possible options of parents (e.g., as represented by the five layers of optimization indicated in FIGS. 3E-3F, at columns ZZ-DDD), for example, by initially selecting a relatively large first set of potential crosses, then applying the models described above to account for genetic diversity and/or risks to select a smaller second set from the first, then reapplying the models to select an even smaller third set of crosses from the second set, and so on until the number of crosses has been sufficiently narrowed, as desired (e.g., five times as indicated in the excerpt 300, etc.). When such iterative process is used, the score matrices P and R defined in Equation (6) and the score vector c defined in Equation (13) can be normalized using Equations (14), (15) and (16) below.

$$\hat{P}_{perf} = \frac{P_{perf} - \min(P_{perf})}{\max(P_{perf}) - \min(P_{perf})} \quad (14)$$

$$\hat{R}_{perf} = \frac{R_{perf} - \min(R_{perf})}{\max(R_{perf}) - \min(R_{perf})} \quad (15)$$

$$\hat{c}_{perf} = \frac{c_{perf} - \min(c_{perf})}{\max(c_{perf}) - \min(c_{perf})} \quad (16)$$

Finally in the method 400, upon selection of the desired ones of the indicated parents, the breeding engine 112 directs the selected parents, and their potential crosses, at 418, to the plant breeding pipeline 102, and in particular, to the initial grow phase 104. For example, in the excerpt 300, selection would be based on the results of the fifth optimization layer, indicated in column DDD of FIG. 3F. Here, none of the crosses would be selected as all included a "FALSE" designation (with a further explanation for the "FALSE" designation then provided in column EEE).

As should now be appreciated, the above systems and methods provide for substantial efficiencies over conventional plant breeding techniques. For a potential cross population, a breeder typically relies on a variety of parameters of the parents to filter ones of the potential crosses, ultimately coming to a number of seed origins (or parents), which are provided to a breeding pipeline (e.g., breeding pipeline 102, etc.). Specifically, for example, in a historical application of the systems and methods herein, 120 potential crosses may have been available for selection to breeders via conventional methods, from available historical data about the parents, to enter a breeding pipeline over each of several recent years, whereby additional resources were then spent processing, testing, and cultivating each of the 120 crosses to arrive at a subset of crosses that were advanced to become commercial products. Through use of the breeding engine 112 described herein, of the 120 potential crosses, 24 were identified and selected (e.g., at 416 in the method 400, etc.) to enter the breeding pipeline. In so doing, the 24 crosses included approximately 69% of the commercially successful crosses that had been selected by the breeder, historically, using conventional techniques, thus providing a substantial efficiency gain (i.e., 24 crosses instead of 120 crosses entering the breeding pipeline).

Moreover, the systems and methods herein employ the commercial success history of parents (and parental lines), in combination with historic trait information, to select seed origins to be introduced to a breeding pipeline. The reliance on multiple different types of data, including the commercial success, the relatedness of the parents, and risk provides a more complete picture of how the seed origins will progress in the breeding pipeline. As such, the role of the breeder's expectations, tendencies and/or assumptions is reduced in the process, resulting in a more efficient capture of the commercially viable seed origins from a substantial number of potential seed origins. Through the systems and methods disclosed herein, breeders can vastly improve their pipelines to identify and select for advancement those hybrids that would otherwise be potentially eliminated when using traditional operations.

Furthermore, the systems and methods herein are not limited geographically, or otherwise, in any way. For example, if a crop can be grown in a given area, the breeding engine herein can be used to recommend an optimal set of crosses to make for that specific market/environment by weighting the data corresponding to certain traits that affect crop performance and/or commercial/market success in that environment. Such environment may be represented globally or regionally, or it may be as granular as a specific location within a filed (such that the same field is identified to have different such environments). In addition, the breeding engine herein may be used to target the development of products specific to certain markets, geographies, soil types, etc., or with directives to, maximize profits, maximize customer satisfaction, minimize production costs, etc.

Figure 8:
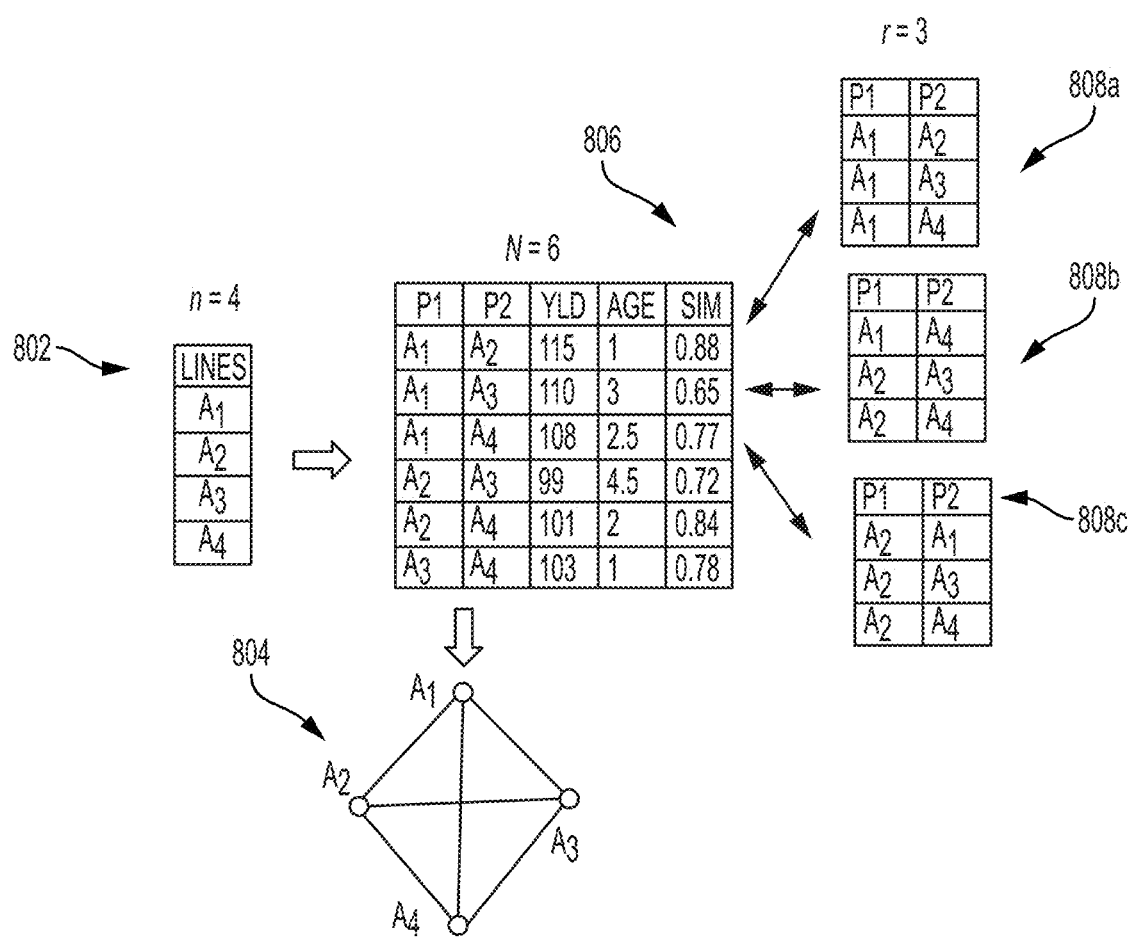
FIG. 8 illustrates an exemplary breeding situation involving selection from among four potential parents.

FIG. 8 provides an exemplary illustration of the above for a given sample set of four parents 802 (i.e., n=4), $A_1, A_2, A_3$, and $A_4$. That said, it should be appreciated that a breeder will typically be provided with hundreds, thousands, hundreds of thousands, etc. parents from which a cross may be selected in large industrial breeding pipelines.

In connection therewith, diagram 804 provides an indication of all the potential crosses of the four parents 802, where a cross is indicated by each connecting line. The potential crosses of the parents 802 is then listed in matrix 806, where N=6. In addition to the listing of the two parents per cross (at P1 and P2), the matrix 806 further includes certain data related to the parents and/or crosses, similar to the data included in excerpt 300, such as, for example, an expected yield for each of the crosses and also an age for each of the crosses, which is indicative of the average age of the parents 802. The matrix 806 further includes a "SIM," or genetic similarity of the parents 802. In a breeding process, where yield is the target phenotype of maize, and only three crosses were to be provided to a plant breeding pipeline (r=3), it should be apparent that some, if not all, conventional breeding methodologies may select the top three crosses in the matrix 806, i.e., the highest yielding crosses. By selecting in this manner, i.e., in the conventional manner, the breeder will select three crosses, which each include the parent $A_1$. This provides reduced genetic diversity in the breeding pipeline (e.g., pipeline 102, etc.), whereby if an issue with the parent $A_1$ is identified, all crosses in the pipeline based on parent $A_1$ are wasted, which in this example is all three. In other words, as demonstrated herein, selecting, in a breeding process, the best crosses, even when yield is the phenotype of interest, does not always mean selecting the crosses with the best expected yield (particularly when genetic diversity is taken into account).

Exemplary numbers indicate the probabilities of selecting the "best" crosses to be included in the breeding pipeline. Specifically, the number of potential crosses for a given set of parents is provided by Equation (17) below:

$$\frac{n(n-1)}{2} \tag{17}$$

So for n=4, in the above example, the number of potential crosses, as indicated above, is 6, i.e., N=6 (as indicated in FIG. 8). Then, the possible number of sets (also referred as cohorts) with the desired number of crosses (i.e., ordered pairs of parents) is provided by Equation (18) below:

$$C_r^N = \frac{N!}{(N-r)!r!} \tag{18}$$

Then, for N=6 and r=3 (i.e., the number of desired crosses to the pipeline, as provided in the above example), the total number of potential cohorts is 20.

In a more practical example, in the context of an industrial breeding process, n may be 1000, while r is 100. By the above Equations (17) and (18), the total potential number of parents would be approximately $10^{400}$. In general, in connection therewith, it may be difficult and/or even not feasible, from a computational complexity and/or resources standpoint, to evaluate each potential cross in terms of diversity, distribution of traits etc., whereby optimal cross could be selected (although this is not conventionally done). Yet, the probability of reaching the optimal cohorts, given the variables, by human selection or conventional methodologies (e.g., without considering genetic diversity, commercial success, etc.), for example, would be $10^3/10^{400}$ or $1/10^{297}$. The systems and methods herein may account for the entire set of potential crosses (in the context of the variables described herein), and therefore would not artificially reduce the set of the potential crosses as potentially made necessary by the computational complexity and/or resources available.

Figure 9:
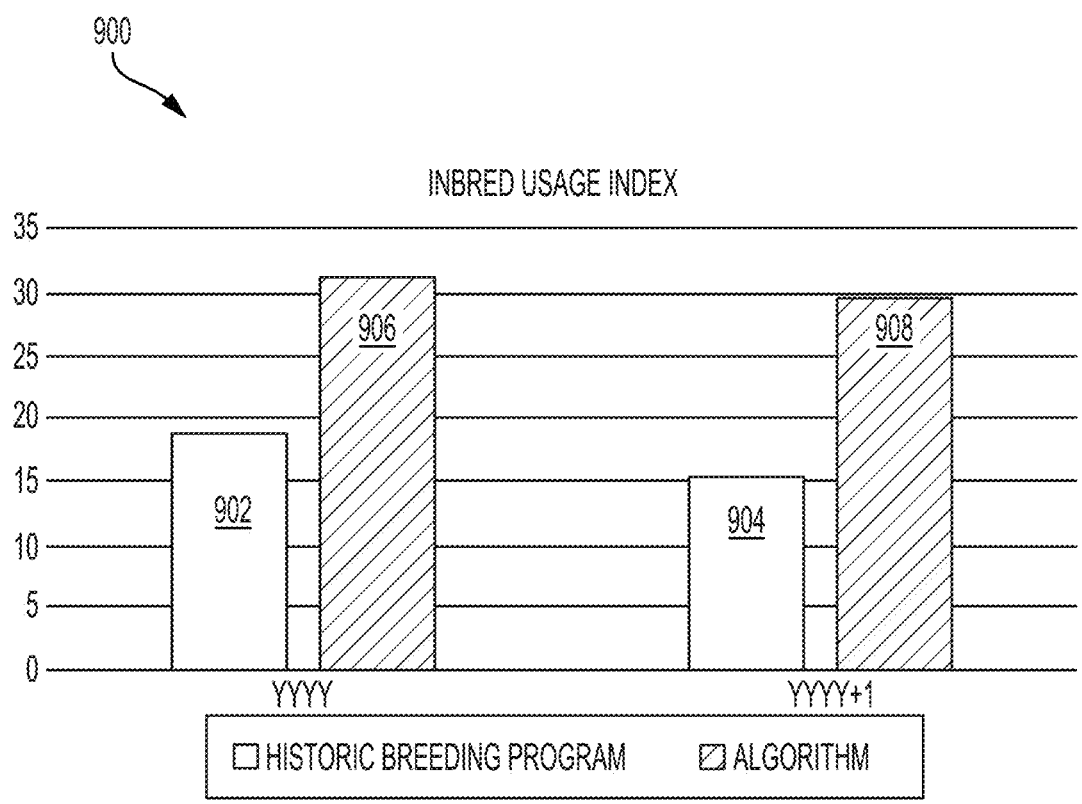
FIG. 9 is an exemplary graphical comparison of example inbred usage indexes (IUIs), based on historical data (as found in a crosses data structure for certain years), for conventional breeding and the exemplary method of FIG. 4.

What's more, with reference to FIG. 9, the systems and methods herein may provide improvement over conventional methods by providing for population level distribution of parental usage (e.g., genetic diversity, etc.). In particular, for example, an inbred usage index (or IUI) is determined, based on Equation (19) below.

$$IUI = 100\% \times \frac{\text{\# of Unique Inbred Lines in Selected Filtered Target Crosses}}{2x \text{\# of set of potential crosses}} \tag{19}$$

In this example, an IUI of 100% would imply that every parent (in the set of potential crosses) is used only once when selecting the filtered target crosses, as described above, or otherwise (e.g., via conventional manual methods, etc.). In contrast, a lower IUI would indicate that one parent or multiple parents are more prevalent (i.e., the lower the IUI, the higher the occurrence of a parent in the selected potential crosses (destined for the breeding pipeline 102, for example)). As shown in FIG. 9, for example, historical data for a conventional breeding method yields the IUI values represented at 902 (IUI value of about 18.86) and 904 (IUI value of about 15.29), for years YYYY and YYYY+1 (one year later), respectively. Conversely, through the systems and methods herein, based upon the data available for those years, the selected filtered target potential crosses would provide the IUI at each of 906 (IUI value of about 31.38) and 908 (IUI value of about 29.72), for the respective years. That is, at least in the context of this example, the IUI for selected filtered target crosses is greater than 20, greater than 25, and/or greater than 30, or other suitable values, etc. As shown, the population level distribution of parental usage is increased substantially over manual conventional breeding methods.

With that said, it should be appreciated that the functions described herein, in some embodiments, may be described in computer executable instructions stored on a computer readable media, and executable by one or more processors. The computer readable media is a non-transitory computer readable media. By way of example, and not limitation, such computer readable media can include RAM, ROM, EEPROM, CD-ROM or other optical disk storage, magnetic disk storage or other magnetic storage device, or any other medium that can be used to carry or store desired program code in the form of instructions or data structures and that can be accessed by a computer. Combinations of the above should also be included within the scope of computer-readable media.

It should also be appreciated that one or more aspects of the present disclosure transform a general-purpose computing device into a special-purpose computing device when configured to perform the functions, methods, and/or processes described herein.

As will be appreciated based on the foregoing specification, the above-described embodiments of the disclosure may be implemented using computer programming or engineering techniques including computer software, firmware, hardware or any combination or subset thereof, wherein the technical effect may be achieved by performing at least one of the following operations: (a) accessing a data structure representative of multiple parents; (b) identifying a set of potential crosses, each potential cross in the set of potential crosses including at least two of the multiple parents included in the data structure; (c) selecting, by at least one computing device, a subgroup of potential crosses, from the set of potential crosses, based on one or more thresholds associated with population prediction scores for the set of potential crosses, each population prediction score associated with a prediction of commercial success for the associated potential cross within the set of potential crosses; (d) selecting, by the at least one computing device, multiple target crosses from the subgroup of potential crosses based on a genetic relatedness of the parents in the subgroup of potential crosses; € filtering, by the at least one computing device, the target crosses based on at least one rule, the at least one rule defining at least one threshold for at least one characteristic and/or trait of at least one of: the multiple target crosses, one of the multiple parents included in the target crosses, and a parental line of the target cross; (f) selecting, by the at least one computing device, ones of the filtered target crosses based on risk associated with the selected one of the filtered target crosses; (g) directing the selected ones of the filtered target crosses into a breeding pipeline, thereby providing crosses to the breeding pipeline based, at least in part, on commercial success of parents included in the selected ones of the filtered crosses; (h) clustering, by the at least one computing device, the parents of the potential crosses included in the subgroup, based on the relatedness of the parents; (i) combining, by the at least one computing device, a cluster score associated with at least one parent of one of the potential crosses included in the subgroup and a cluster score associated with said one of the potential crosses; and (j) generating the population prediction scores for each potential cross within the set of potential crosses.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. In addition, advantages and improvements that may be achieved with one or more exemplary embodiments disclosed herein may provide all or none of the above mentioned advantages and improvements and still fall within the scope of the present disclosure.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When a feature is referred to as being "on," "engaged to," "connected to," "coupled to," "associated with," "in communication with," or "included with" another element or layer, it may be directly on, engaged, connected or coupled to, or associated or in communication or included with the other feature, or intervening features may be present. As used herein, the term "and/or" includes any and all combinations of one or more of the associated listed items.

Although the terms first, second, third, etc. may be used herein to describe various features, these features should not be limited by these terms. These terms may be only used to distinguish one feature from another. Terms such as "first," "second," and other numerical terms when used herein do not imply a sequence or order unless clearly indicated by the context. Thus, a first feature discussed herein could be termed a second feature without departing from the teachings of the example embodiments.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for use in identifying crosses for use in plant breeding, the method comprising:
   accessing a data structure representative of multiple parents;
   identifying a set of potential crosses, each potential cross in the set of potential crosses including ones of the multiple parents included in the data structure;
   generating, by the at least one computing device, population prediction scores for each potential cross within the set of potential crosses, each population prediction score including a prediction of commercial success for the potential cross, based on historical advancement of at least one of the parents of the potential cross for commercialization;
   selecting, by at least one computing device, a subgroup of potential crosses, from the set of potential crosses, based on one or more thresholds associated with the population prediction scores for the set of potential crosses;
   selecting, by the at least one computing device, multiple target crosses from the subgroup of potential crosses based on a genetic relatedness of the parents in the subgroup of potential crosses and a risk associated with the multiple target crosses; and
   directing ones of the selected multiple target crosses into a breeding pipeline, thereby providing crosses to the breeding pipeline based, at least in part, on commercial success of parents included in the ones of the selected multiple target crosses.

2. The method of claim 1, wherein generating the population prediction scores includes generating, by the at least one computing device, the population prediction scores based on the following algorithm:

$$p(s_i|x_i,D)=\Sigma_{m=1}^{M}p(s_i|x_i,m,D)p(m|D).$$

3. The method of claim 1, wherein selecting the multiple target crosses from the subgroup of potential crosses based on the genetic relatedness includes:
   clustering, by the at least one computing device, the parents of the potential crosses included in the subgroup, based on the relatedness of the parents; and
   wherein selecting the multiple target crosses is based on a relatedness threshold associated with the clustered parents of the target crosses.

4. The method of claim 3, wherein clustering the parents includes spectral clustering, by the at least one computing device, of the parents of the potential crosses included in the subgroup; and
   wherein selecting the multiple target crosses includes:
      combining, by the at least one computing device, a cluster score associated with at least one parent of one of the potential crosses included in the subgroup and a cluster score associated with said one of the potential crosses; and
      selecting the multiple target crosses based on a comparison of the combined cluster scores to the relatedness threshold.

5. The method of claim 1, wherein selecting the multiple target crosses from the subgroup of potential crosses is further based on at least one rule is associated with at least one of stalk lodging, root lodging, Goss Wilt, parental similarity, and a difference between expected relative maturity (ERM) between the two parents.

6. The method of claim 1, wherein selecting the multiple target crosses based on risk includes determining, by the at least one computing device, risks associated with the potential crosses based on a quadratic algorithm dependent on a risk variable, a diversity variable, and a performance variable of the crosses.

7. The method of claim 6, wherein determining the risks includes determining the risks, by the at least one computing device, based on the following algorithm(s):

$$x_{OPT} = \operatorname{argmax} \lambda_{perf}(c^T x + x^T P x) - \frac{1}{2}(\lambda_{risk} x^T R x + \lambda_{div} x^T S x)$$

$$\text{subject to } \sum x_i = 1, \ x_i \geq 0 \ \forall \ i \text{ and}$$

$$\sum_{x_i \in F} x_i \geq 0.4 \text{ and } \sum_{x_i \in M} x_i \geq 0.4.$$

8. The method of claim 6, wherein the risk variable of the quadratic algorithm associated with the ones of the target crosses accounts for risk associated with multiple characteristics and/or traits of the cross.

9. The method of claim 1, further comprising planting one or more plants in a growing space of a breeding pipeline, the plant derived from the ones of the selected multiple target crosses.

10. The method of claim 1, wherein selecting the multiple target crosses from the subgroup of potential crosses based on a genetic relatedness of the parents in the subgroup of potential crosses includes selecting the multiple target crosses to satisfy a genetic diversity criterion among the parents of the selected multiple target crosses.

11. A system for use in identifying crosses for use in plant breeding, the system comprising:
   a crosses data structure including multiple parents available for use in crosses in plant breeding, and a set of potential crosses, each potential cross in the set of potential crosses including ones of the multiple parents;
   a computing device coupled in communication with the data structure and configured to:
      generate population prediction scores for each potential cross within the set of potential crosses, based on:

$$p(s_i \mid x_i, D) = \sum_{m=1}^{M} p(s_i \mid x_i, m, D) p(m \mid D),$$

where each population prediction score includes a prediction of commercial success for the potential cross, based on historical advancement of at least one of the parents of the potential cross for commercialization;
      select a subgroup of potential crosses from the set of potential crosses, in the data structure, based on one or more thresholds associated with the population prediction scores for the potential crosses;
      select multiple target crosses, from the subgroup of potential crosses, based on genetic relatedness of the parents of the subgroup of potential crosses and risk associated with the multiple target crosses; and
      direct ones of the selected multiple target crosses into a breeding pipeline, thereby providing crosses to the breeding pipeline based, at least in part, on commercial success of parents to the ones of the selected multiple target crosses.

12. The system of claim 11, further comprising the breeding pipeline coupled in communication with the computing device; and
   wherein the breeding pipeline includes a growing space and one or more plants derived from at least one of the selected multiple target crosses planted in the growing space, after the ones of the selected multiple target crosses are directed to the breeding pipeline.

13. The system of claim 11, wherein the computing device is configured, in order to select the multiple target crosses, to cluster the parents of the potential crosses included in the subgroup, based on the relatedness of the parents of the potential crosses, and then to select the multiple target crosses from the subgroup of potential crosses based on a relatedness threshold associated with the clustered parents of the target crosses.

14. The system of claim 11, wherein the computing device is further configured to identify, based on a user input, the set of potential crosses.

15. The system of claim 11, wherein the computing device is configured to select the multiple target crosses from the subgroup of potential crosses further based on at least one rule is associated with at least one of stalk lodging, root lodging, Goss Wilt, parental similarity, and a difference between expected relative maturity (ERM) between the two parents.

16. The system of claim 11, wherein the computing device is further configured to determine risks associated with the crosses based on a quadratic algorithm dependent on a risk variable, a diversity variable, and a performance variable of the crosses.

17. The system of claim 11, wherein the computing device is further configured, in order to select based on risk associated, to determine the risks associated with the crosses based on:

$$x_{OPT} = \mathrm{argmax}\, \lambda_{perf}\left(c^T x + x^T P x\right) - \frac{1}{2}\left(\lambda_{risk} x^T R x + \lambda_{div} x^T S x\right)$$

subject to $\sum x_i = 1$, $x_i \geq 0\, \forall\, i$ and $\sum_{x_i \in F} x_i \geq 0.4$ and $\sum_{x_i \in M} x_i \geq 0.4$.

18. The system of claim 11, wherein the computing device is configured to select the multiple target crosses from the subgroup of potential crosses further based on a genetic diversity criterion across the selected multiple target crosses.

19. A non-transitory computer readable storage medium including executable instructions for use in identifying crosses for use in plant breeding, which, when executed by at least one processor, causes the at least one processor to:
    access a data structure representative of multiple parents;
    identify a set of potential crosses, each potential cross in the set of potential crosses including ones of the multiple parents included in the data structure;
    generate population prediction scores for each potential cross within the set of potential crosses, each population prediction score including a prediction of commercial success for the potential cross, based on historical advancement of at least one of the parents of the potential cross for commercialization;
    select a subgroup of the set of potential crosses based on one or more thresholds associated with the population prediction scores for the potential crosses;
    select multiple target crosses from the subgroup of potential crosses based on at least: genetic relatedness of the parents of the subgroup of potential crosses and risk associated with the subgroup of potential crosses; and
    direct ones of the multiple target crosses into a breeding pipeline, thereby providing crosses to the breeding pipeline based, at least in part, on commercial success of parents to the ones of the multiple target crosses.

20. The non-transitory computer readable storage medium of claim 19, wherein the executable instructions, when executed by at least one processor, cause the at least one processor, in selecting the multiple target crosses from the subgroup of potential crosses based on a genetic relatedness, to select the multiple target crosses based on the parents of the multiple target cross satisfying a genetic diversity criterion for the breeding pipeline.

* * * * *